`US008552139B2`

(12) United States Patent
Bezwada

(10) Patent No.: US 8,552,139 B2
(45) Date of Patent: Oct. 8, 2013

(54) CONTROLLED RELEASE OF BIOLOGICALLY ACTIVE COMPOUNDS

(75) Inventor: Rao S Bezwada, Hillsborough, NJ (US)

(73) Assignee: Bezwada Biomedical LLC, Hillsborough, NJ (US)

( * ) Notice: Subject to any disclaimer, the term of this patent is extended or adjusted under 35 U.S.C. 154(b) by 0 days.

(21) Appl. No.: 13/484,391

(22) Filed: May 31, 2012

(65) Prior Publication Data

US 2013/0142752 A1    Jun. 6, 2013

Related U.S. Application Data

(62) Division of application No. 12/202,939, filed on Sep. 2, 2008, now Pat. No. 8,217,134.

(60) Provisional application No. 60/968,917, filed on Aug. 30, 2007.

(51) Int. Cl.
*C08G 63/02* (2006.01)

(52) U.S. Cl.
USPC ....... 528/74.5; 528/272; 424/426; 514/772.3; 523/105; 523/113

(58) Field of Classification Search
USPC ............... 528/74.5, 272; 424/426; 514/772.3; 523/105, 113
See application file for complete search history.

(56) References Cited

U.S. PATENT DOCUMENTS

| | | | |
|---|---|---|---|
| 3,044,942 A | 7/1962 | Baptist | |
| 3,297,033 A | 1/1967 | Schmitt | |
| 3,371,069 A | 2/1968 | Miyamae | |
| 3,531,561 A * | 9/1970 | Michel | ....................... 264/210.4 |
| 3,636,956 A | 1/1972 | Schneider | |
| 4,052,988 A | 10/1977 | Doddi | |
| 4,130,639 A | 12/1978 | Shalaby | |
| 4,532,928 A | 8/1985 | Bezwada | |
| 4,605,730 A | 8/1986 | Shalaby | |
| 4,653,497 A | 3/1987 | Bezwada | |
| 4,689,424 A | 8/1987 | Shalaby | |
| 4,829,099 A | 5/1989 | Fuller | |
| 4,886,870 A | 12/1989 | D'Amore | |
| 4,938,949 A | 7/1990 | Barch | |
| 5,082,925 A | 1/1992 | Shalaby | |
| 5,264,540 A | 11/1993 | Cooper | |
| 5,521,431 A | 5/1996 | Tahara | |
| 5,759,830 A | 6/1998 | Vacanti | |
| 5,801,033 A | 9/1998 | Hubbell | |
| 5,834,274 A | 11/1998 | Hubbell | |
| 5,834,513 A | 11/1998 | Ptchelintsev | |
| 5,843,743 A | 12/1998 | Hubbell | |
| 5,895,150 A | 4/1999 | Watabe | |
| 5,902,599 A | 5/1999 | Anseth | |
| 5,932,229 A | 8/1999 | Ptchelintsev | |
| 5,942,252 A | 8/1999 | Tice | |
| 5,951,997 A | 9/1999 | Bezwada | |
| 6,468,519 B1 | 10/2002 | Uhrich | |
| 6,689,350 B2 | 2/2004 | Uhrich | |
| 6,773,721 B1 | 8/2004 | Wong | |
| 6,861,068 B2 | 3/2005 | Ng | |
| 6,869,615 B2 | 3/2005 | Chen | |
| 6,887,974 B2 | 5/2005 | Pathak | |
| 6,890,561 B1 | 5/2005 | Blatt | |
| 2002/0169275 A1 | 11/2002 | Matsuda | |
| 2003/0158598 A1 | 8/2003 | Ashton | |
| 2003/0216307 A1 | 11/2003 | Kohn | |
| 2003/0232091 A1 | 12/2003 | Shefer | |
| 2004/0096476 A1 | 5/2004 | Uhrich | |
| 2004/0117007 A1 | 6/2004 | Whitbourne | |
| 2005/0048121 A1 * | 3/2005 | East et al. | ...................... 424/486 |
| 2005/0074493 A1 | 4/2005 | Mehta | |
| 2005/0095300 A1 | 5/2005 | Wynn | |
| 2005/0112171 A1 | 5/2005 | Tang | |
| 2005/0152958 A1 | 7/2005 | Cordes | |
| 2005/0238689 A1 | 10/2005 | Carpenter | |
| 2006/0013851 A1 | 1/2006 | Giroux | |

FOREIGN PATENT DOCUMENTS

| | | | |
|---|---|---|---|
| WO | 97/39738 | A2 | 10/1997 |
| WO | 98/36013 | A1 | 4/1998 |
| WO | 99/12990 | A1 | 3/1999 |
| WO | 99/29885 | A1 | 6/1999 |
| WO | 01/41753 | A2 | 6/2001 |
| WO | 02/09767 | A2 | 2/2002 |
| WO | 02/09768 | A2 | 2/2002 |
| WO | 2004/008101 | A2 | 1/2004 |
| WO | 2006/052790 | A2 | 5/2006 |

OTHER PUBLICATIONS

J. Org. Chem, 1959, 24, 523-526.
Gutowska eta!, J. Biomater. Res., 29,811-21 (1995).
Hoffman, J. Controlled Release, 6, 297-305 (1987).
Mikos et al, Biomaterials, 14, 323-329 (1993).
Shugens et al, J. Biomed. Mater. Res., 30, 449-462 (1996).
Bulletin of the Material Research Society, Special Issue on Tissue Engineering (Guest Editor: Joachim Kahn), 21 (11), 22-26 (1996).
Remington's Pharmaceutical Sciences, 18m ed., Mack Publishing Company, Eason, PA, 1990, p. 1445.
Langer, R., Science 249: 1527-1533 (1990).
van Dijk-Wolthuis, W.N.W. "Degradation and Release Behavior of Dextran-Based Hydrogels", Macromolecules, 30; (1997) 4639-4645.
van Dijk-Wolthuis, W.N.E.; "A new class of polymerizable dextrans with hydrolysable groups: hydroxyethyl methacrylated dextran with and without oligolactate spacer", Polymer, 38 (25); (1997) 6235-6242.
Kurisawa et al, Macromol. Chem. Phys. 199, 705-709 (1998).
Heller, J.; Helwing, R.F.; Baker, R.W.; and Tuttle, M.E. "Controlled release of water-soluble macromolecules from bioerodible hydrogels" Biomaterials, 4; (1983) 262-266.
Brondsted (Brondsted, H.; and Kopccek, J. "Hydrogels for site-specific oral drug delivery: synthesis and characterization" Biomaterials, 12; (1991) 584-592.
Ulbrich, K.; "Novel biodegradable hydrogels prepared using the divinylic crosslinking agent N, 0-dimethacryloylhydroxylamine 1. Synthesis and characterization of rates of gel degradation, and rate of release of model drugs, in vitro and in vivo" Journal of Controlled Release, 24; (1993) 181-190.

* cited by examiner

*Primary Examiner* — Ling Choi
*Assistant Examiner* — Chun-Cheng Wang
(74) *Attorney, Agent, or Firm* — Vance Intellectual Property, PC

(57) ABSTRACT

The present invention relates to biodegradable polymers (e.g., polyesters and polyester amides) derived from functionalized biologically active compounds that can provide site specific delivery of bioactive compounds upon biodegradation in a controlled manner.

30 Claims, No Drawings

CONTROLLED RELEASE OF BIOLOGICALLY ACTIVE COMPOUNDS

CROSS REFERENCE TO RELATED APPLICATIONS

This application claims the benefit of U.S. Application No. 60/968,917, filed Aug. 30, 2007, the disclosure of which is hereby incorporated herein by reference in its entirety.

FIELD OF THE INVENTION

This invention is based on the discovery of new class of biodegradable polymers derived from functionalized biologically active compounds that can provide site specific delivery of bioactive compounds upon biodegradation in a controlled manner.

BACKGROUND OF THE INVENTION

Biologically active compounds are well known (e.g., aspirin and capsaicin) and have been beneficially administered to patients in need thereof for more than a century. One problem that has been associated with many biologically active compounds is that they can be difficult to dissolve in water or the human body and can also be very difficult to polymerize. Due to the availability and numerous uses of biologically active compounds, it is desirable to enhance their native value by, for example, providing compounds or combinations of compounds with a specific controlled degradation profile or range enabling controlled release of the biologically active compound over an extended, controllable time range.

Polymers prepared from aromatic compounds such as terephthalic acid, p-aminobenzoic acid, and p-phenylenediamine exhibit excellent physical properties, but the polymers are not biodegradable. Polyesters derived from terephthalic acid, such as polyethylene terephthalate (PET), polytrimethylene terephthalate (PTT), and poly(1,4-butylene terephthalate) (PBT) are used extensively for making fibers and molding articles. Some of these are polymers that are used in biomedical applications such as non-absorbable surgical sutures, and these polymers are considered to be safe and biocompatible. Unfortunately, these polymers are non-absorbable and, therefore, cannot be used as absorbable sutures or as absorbable polymers for the controlled release of drugs.

Due to the availability and numerous uses of the polymers derived from these aromatic compounds, it is desirable to enhance their value, for example, by functionalizing these aromatic compounds and preparing absorbable polymers therefrom. The resulting absorbable polymers should have a controlled degradation profile or range enabling controlled release of drugs over an extended, controllable time range when physically admixed with these polymers.

Synthetic absorbable polymers have been used to produce various surgical products such as sutures, implants, prostheses, and the like, for several years. Illustrative U.S. patents describing such polymers include U.S. Pat. Nos. 3,297,033, 3,044,942, 3,371,069, 3,531,561, 3,636,956, Re. 30,170, and 4,052,988.

Polyesters are used routinely by those skilled in the art in various drug delivery systems. For example, U.S. Pat. No. 5,942,252 describes a microcapsule comprising as its biocompatible excipient a poly(lactide-co-glycolide), poly(lactide), poly(glycolide), copolyoxalate, polycaprolactone, poly(lactide-co-caprolactone), poly(esteramide), polyorthoester, poly(p-hydroxybutyric) acid and/or polyanhydride which is disclosed as being useful in delivering antigens or vaccines into and through mucosally-associated lymphoid tissue.

WO 99/29885 describes a process which is disclosed as being useful for degrading poly(ester-amides) and poly(ester-urethanes) encapsulating chemicals, drugs, enzymes, microorganisms and seeds by introducing the polymer to an aqueous nutrient solution and inoculating the solution with a culture containing a selected bacteria.

WO 98/36013 describes aliphatic-aromatic dihydroxy compounds which are disclosed as being useful as controlled drug delivery systems.

WO 97/39738 describes the preparation of microparticles which are disclosed as comprising a sustained release ionic conjugate including a free carboxyl group containing biodegradable polymers and a free amino group-containing drug.

U.S. Pat. No. 5,264,540 describes aromatic polyanhydrides which are disclosed as being biocompatible and biodegradable and which are prepared from para-substituted bis-aromatic dicarboxylic acids for use on wound closure devices. However, these compounds exhibit high melt and glass transition temperatures and decreased solubility, thus making them difficult to process. The disclosed polyanhydrides also comprise radical or aliphatic bonds that cannot be hydrolyzed by water.

Polyanhydride polymeric matrices have also been described for use in orthopedic and dental applications. For example, U.S. Pat. No. 4,886,870 describes an article that is disclosed as being bioerodible and useful for prosthesis and implantation that comprises a biocompatible, hydrophobic polyanhydride matrix. U.S. Pat. No. 5,902,599 describes polymer networks which are formed by polymerizing anhydride prepolymers and which are disclosed as being biodegradable and useful in a variety of dental and orthopedic applications.

It would be desirable to identify methods and compositions for effectively delivering biologically active compounds in a controlled and modifiable fashion. The present invention is directed to these, as well as other important ends.

SUMMARY OF INVENTION

The present invention is based on the discovery of a new class of biodegradable polymers, derived from functionalized biologically active compounds that can provide site-specific delivery of bioactive compounds upon degradation in a controlled manner. By varying the functionalizing moiety or combination of moieties, the rate of biodegradation may be varied over a period of time, for example, from about one month to about four years, and may be selected as desired, depending on the end-use.

In certain preferred embodiments of the invention, the biodegradable polyesters have the formula III, VI, or XI, or biodegradable polyamide esters have formula VIII or IX, or pharmaceutically acceptable salts thereof:

(A)

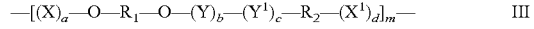
$\quad$ III wherein the polyester of formula III is formed by condensation polymerization of monomers of formula I and II:

$\quad$ I

$\quad$ II (B)

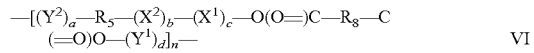
$\quad$ VI wherein the polyester of formula IV is formed by condensation polymerization of monomers of formula IV and V:

$$R_6{-}(Y^2)_a{-}R_5{-}(X^2)_b{-}R_7 \quad\quad IV$$

$$H{-}(X^1)_c{-}O(O{=})C{-}R_8{-}C({=}O)O{-}(Y^1)_d{-}H \quad\quad V$$

(C)

$$\begin{aligned}&-[(X^1)_c{-}O(O{=})C{-}R_9{-}C({=}O)O{-}(Y^1)_d{-}(Y^2)_a\\&-CH_2(O{=})C{-}NH{-}R_{10}{-}NH{-}C({=}O)\\&CH_2{-}(X^2)_b]_o{-} \quad\quad VIII\end{aligned}$$

wherein the polyamide ester of formula VIII is formed by condensation polymerization of monomers of formula Va and VII:

$$H{-}(X^1)_c{-}O(O{=})C{-}R_9{-}C({=}O)O{-}(Y^1)_d{-}H \quad\quad Va$$

$$R_{11}{-}(Y^2)_a{-}CH_2(O{=})C{-}NH{-}R_{10}{-}NH{-}C({=}O)CH_2{-}(X^2)_b{-}R_{12} \quad\quad VII$$

(D)

$$\begin{aligned}&-[(X)_a{-}O{-}R_1{-}O{-}(Y)_b{-}(Y^2)_a{-}CH_2(O{=})C{-}\\&NH{-}R_{10}{-}NH{-}C({=}O)CH_2{-}(X^2)_b]_p{-} \quad\quad IX\end{aligned}$$

wherein the polyamide ester of formula IX is formed by condensation polymerization of monomers of formula I and VII:

$$H{-}(X)_a{-}O{-}R_1{-}O{-}(Y)_b{-}H \quad\quad I$$

$$R_{11}{-}(Y^2)_a{-}CH_2(O{=})C{-}NH{-}R_{10}{-}NH{-}C({=}O)CH_2{-}(X^2)_b{-}R_{12} \quad\quad VII$$

(E)

$$[-(Y)_e{-}R_{13}{-}C({=}O)O{-}(Y)_f{-}]_q{-} \quad\quad XI$$

wherein the polyester of formula XI is formed by self condensation polymerization of a monomer of formula X:

$$R_{14}{-}(Y)_e{-}R_{13}{-}C({=}O)O{-}(Y)_f{-}H \quad\quad X$$

wherein:

m, n, o, p, and q are each independently an integer from about 5 to about 1000;

$R_1$, $R_5$, $R_9$, and $R_{13}$ are each independently the remaining portion of a biologically active compound;

$R_2$, $R_8$, and $R_{10}$ are each independently the remaining portion of a biologically active compound or non-biologically active compound;

$R_3$, $R_4$, $R_6$, $R_7$, $R_{11}$, $R_{12}$, and $R_{13}$ are each independently selected from Cl, F, Br, and I;

X, $X^1$ and $X^2$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;

Y, $Y^1$, and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;

each y and z is independently an integer from about 2 to about 24;

each a, b, c, and d is independently an integer from about 1 to about 6;

each e is independently an integer from about 1 to about 6; and each f is independently an integer from about 0 to about 6.

The present invention also provides a method of preparing absorbable polymer compositions comprising one or more functionalized biologically active compounds and a pharmaceutically acceptable carrier.

The present invention also provides a therapeutic method for treating a disease in a mammal comprising administering to a mammal in need of such therapy, an effective amount of a polymer of the present invention.

The present invention also provides a method of delivering a biologically active compound to a mammal comprising administering to the mammal a biocompatible and biodegradable polymer of the present invention, which degrades to release one or more biologically active compounds.

The present invention also provides a polymer for use in medical therapy, as well as the use of a polymer of the present invention for the manufacture of a medicament useful for the treatment of a disease in a mammal.

The invention also provides processes of functionalizing biologically active compounds and preparation of biologically active polymers with controlled degradation profiles.

DETAILED DESCRIPTION OF THE PRESENT INVENTION

As used herein, the term "biologically active compound" refers to a naturally occurring, semi-synthetic, or synthetic agent that provides a pharmaceutically, therapeutically and/or physiologically desirable effect when administered to a mammal (e.g., human). Biologically active compounds capable of incorporation into polymers of the present invention possess at least two functional groups that may each be incorporated into a linkage of the present polymers, for example, an ester or amide linkage such that, upon hydrolysis of the polymer, the biologically active compound is obtained and/or released in a therapeutically effective form. In preferred embodiments, biologically active compounds that may be useful in the present invention have at least one aryl or heteroaryl ring and at least one hydroxyl (OH), substituted or unsubstituted amino, or carboxylic acid substituent on the aromatic or heteroaromatic ring, or functional derivatives of such substituents, such as esters, amides, methyl ethers, and/or glycosides, or other derivatives that would be apparent to those skilled in the art, once placed in possession of the present disclosure.

The biologically active compounds may also comprise other functional groups (e.g., hydroxyl groups, amine groups, and carboxylic acid groups) that may be used to modify properties of the polymer (e.g. for branching, cross linking and/or appending other molecules (e.g. another biologically active compound) to the polymer, for changing the solubility of the polymer, or for effecting the biodistribution of the polymer). Exemplary therapeutic agents that may be employed as the biologically active compounds in the polymers of the present invention may be found, for example, in: Physicians' Desk Reference, 61st Ed., 2007, Thomson Healthcare Company; USPN Dictionary of USAN and International Drug Names, 2000, The United States Pharmacopoeia Convention, Inc., Rockville, Md.; and The Merck Index, 14th Ed., 2007, John Wiley & Sons, the disclosures of each of which are hereby incorporated herein by reference, in their entireties. One skilled in the art can readily select therapeutic agents that possess the necessary functional groups for incorporation into the polymers of the invention from these sources, once placed in possession of the teachings in the present disclosure.

Therapeutic agents that may be incorporated into the monomers, oligomers or polymers of the present invention include, for example, suitably functionalized analgesics or general or local anesthetics, anti-convulsants, anti-diabetic agents, anti-fibrotic agents, anti-infectives, anti-bacterials, anti-fungals, anti-neoplastics, cardioprotective agents, cardiovascular agents, anti-thrombotics, central nervous system stimulants, cholinesterase inhibitors, contraceptives, deodorants, dopamine receptor agonists, erectile dysfunction agents, fertility agents, gastrointestinal agents, gout agents, hormones, immunomodulators, immunosuppressive, migraine agents, non-steroidal anti-inflammatory drugs (NSAIDs), motion sickness agents, muscle relaxants, nucleoside analogs, neurodegenerative agents (e.g., Parkinson's disease), obesity agents, ophthalmic agents, osteoporosis agents, parasympatholytics, parasympathommetics, anti-anesthetics, prostaglandins, psychotherapeutic agents, respiratory agents, sedatives, hypnotics, skin and mucous membrane agents, smoking cessation agents, sympatholytics, urinary tract agents, vaginal agents, and vasodilators, and the like (see Physicians' Desk Reference, 61$^{st}$ Ed., 2007, Thomson Health Care, the disclosures of which are hereby incorporated herein by reference, in their entireties).

Suitable biologically active compounds include, for example, phenolic compounds. Phenol is the simplest example of a phenolic compound, but in preferred embodiments, the phenolic compound has two or more hydroxyl groups. Such phenolic compounds in many instances are bioactive substances which occur widely in food plants that are eaten regularly by substantial numbers of animals and people. These food-plant bioactive phenolic compounds have typically been found to be safe compounds. Included in the definition of biologically active phenolics are highly substituted poly-phenols whose structures include condensed rings.

Examples of naturally occurring biologically active phenolics include bergaptol, caffeic acid, capsaicin, coumarin, daidzein, 2,5-dihydroxy-benzoic acid, ferulic acid, flavonoids, glycitein (isoflavone), 4-hydroxycinnamic acid, 4-hydroxy-coumarin, isopimpinellin, resveratrol, sinapic acid, vanillic acid, and vanillin, and derivatives thereof.

Capsaicin is a biologically active phenolic that is the active component of cayenne pepper. Capsaicin is an amide of vanillylamine and $C_8$ to $C_{13}$ branched fatty acids and may be a powerful pain reliever. In this regard, topical application of capsaicin stimulates and blocks small pain fibers by depleting them of the neurotransmitter substance P that mediates pain impulses. A cream made, for example, from about 0.025% to about 0.075% capsaicin applied 4 times daily may help peripheral neuropathic pain, post-herpetic neuralgia, trigeminal neuralgia, psoriasis and fibromyalgia. It may also be useful for diabetic neuropathy, cluster headaches, earache, osteo- and rheumatoid arthritis.

Naproxen, paracetanol, acetaminophen and acetylsalicylic acid are biologically active phenolics that belong to the class of drugs referred to as non-steroidal anti-inflammatory drugs or NSAIDs. It is generally believed that NSAIDs provide relief by blocking the action of prostaglandins, which are hormone-like substances that contribute to pain, inflammation, fever and muscle cramps.

Phenolic moieties, both synthetic and naturally occurring, are included in many drugs. Examples of these medicinals include acenocoumarol, acetarsol, actinoquinol, adrenalone, alibendol, amodiaquine, anethole, balsalazide, bamethan, benserazide, bentiromide, benzarone, benzquinamide, bevantolol, bifluranol, buclosamide, buphenide, chlorotrianisene, chloroxylenol, cianidanol, cinepazide, cinitapride, cinepazide, cinmetacin, clebopride, clemastine, clioquinol, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoum-acetate, etilefrine, etiroxate, exalamide, exifone, fendosal, fenoldopam mesilate, fenoterol, fenoxedil, fenticlor, flopropione, floredil, fluorescein, folescutol, formo-terol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indomethacin, ipriflavone, isoetarine, isoprenaline, isoxsuprine, itopride hydrochlor-ide, ketobemidone, khellin, labetalol, lactylphenetidin, levodopa. levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxo-line, norfenefrine, normolaxol, octopamine, omeprazole, orciprenaline, oxilofrine, oxitriptan, oxyfedrine, oxypertine, oxyphenbutazone, oxyphenisatin acetate, oxyquinoline, papaverine, paracetanol, parethoxycaine, phenacaine, phenacetin, phenazocine, phenolphthalein, phenprocoumon, phentolamine, phloedrine, picotamide, pimobendan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theo-drenaline, tioclomarol, tioxolone, α-tocopherol (vitamin E), tofisopam, tolcapone, tolterodine, tranilast, tretoquinol, triclosan, trimazosin, trimetazidine, trimethobenz-amide, trimethoprim, trimetozine, trimetrexate glucuronate, troxipide, verapamil, vesnarinone, vetrabutine, viloxazine, warfarin, xamoterol.

Other bioactive phenolics include acacetin, 4-acetamido-2-methyl-1-naphthol, acet-aminophen, albuterol, allenolic acid, aloe emodin, aloin, β-amino-4-hydroxy-3,5-di-iodohydrocinnamic acid, N-(5-amino-2-hydroxyphenyl)-benzene-acetamide, 4-amino-1-naphthol, 3-aminosalicylic acid, 4-aminosalicylic acid, anacardic acid, p-anol, anthragallol, anthralin, anthranol, anthrarobin, anthrarufin, apigenin, apiin, apocynin, aspidinol, aspirin, baptigenin, benzestrol, benzoresorcinol, bisphenol a, bisphenol b, butylated hydroxylanisole, butylated hydroxytoluene, capobenic acid, trans-1-(3'-carboxy-4'-hydroxyphenyl)-2-(2",5"-dihydroxyphenyl)ethane, catechin, chlorogenic acid, m-chlorophenol, 5-chloro-8-quinolinol, chloroxylenol, chlorquinaldol, chromo-nar, chrysin, cinametic acid, clorophene, coniferyl alcohol, p-coumaric acid, coumes-trol, coumetarol, daphnetin, datiscetin, deoxyepinephrine, 3,5-diiodothyronine, 3,5-di-iodotyro sine, dimethophrine, diosmetin, diresorcinol, disoprofol, dopa, dopamine, drosophilin a, efloxate, ellagic acid, embelin, Equol, eriodictyol, esculetin, esculin, ethylnorepinephrine, ethyl vanillin, eugenol, eupatorin, fenadiazole, ferulic acid, fisetin, 3-fluoro-4-hydroxyphenylacetic acid, fraxetin, fustin, galangin, gallacetophe-none, gallic acid, gardenins, genistein, gentisyl alcohol, gepefrine, geranylhydroqui-none, [6]-gingerol, gossypol, guaiacol, guaifenesin, harmalol, hematoxylin, hinderin, homoeriodictyol, homogentisic acid, homovanillic acid, hydroxyamphetamine, 2-hyd-roxy-5-(2,5-dihydroxybenzylamino)-2-hydroxybenzoic acid, 4-hydroxy-3-methoxy-mandelic acid, n-(p-hydroxyphenyl)glycine, hydroxyprocaine, 8-hydroxyquinoline, hypericin, irigenin, isoproterenol, isoquercitrin, isothebaine, kaempferol, liothyronine, luteolin, mangostin, 5,5'-methylenedisalicylic acid, n-methylepinephrine, metyrosine, morin, mycophenolic acid, myricetin, naringenin, nylidrin, orcinol, osalmid, osthole, oxantel, paroxypropione, pentachlorophenol, 3-pentadecylcatechol, p-pentyloxy-phenol, phloretin, phloroglucinol, pinosylvine, plumbagin, pyrocatechol, pyrogallol, quercetagetin, quercetin, resacetophenone, rhamnetin, rhein, sakuranetin, salicyl alcohol, salicylanilide, 4-salicyloylmorpholine, salsalate, scopoletin, scutellarein, serotonin, (3,4,5-trihydroxyphenyl)methylenepropanedinitrile, thymol, thyropropic acid, thyroxine, tiratricol, tyrosine, vanillic acid, and vanillin.

Examples of biologically active amino compounds include Aceclofenac, Acedia-sulfone, Alminoprofen, Amisulpride, AmLexanox, Amodiaquine, Amosulalol, Amoxicillin, Amsacrine, Anileridine, Azacyclonol, Baccofen, Balsalazide sodium, Benzocaine, Bromopride, Bumetanide, Carprofen, Carvedilol, Carzenide, Cefprozil, Cinitapride, Clebopride, Clenbuterol, Diclofenac, Ethoxzolamide, Flufenamic acid, Furosemide, Iobenzamic acid, Iocetamic acid, Mefenamic acid, Nadoxolol, D-Nor-pseudoephedrine and paracetamol.

Examples of biologically active carboxylic acid compounds include Acemetacin, Aceclofenac, Acediasulfone, Adipiodone, Alminoprofen, AmLexanox, Anileridine, Baccofen, Balsalazide sodium, Bentiromide, Benzocaine, Bumetanide, Carprofen, Carzenide, Cinmetacin, Clometacin, Cromoglicic acid, Diclofenac, Diflunisal, Eprosartan, Fendosal, Flufenamic acid, Furosemide, Indometacin, Iobenzamic acid, Iocarmic acid, Iocetamic acid, Iodoxamic acid, Ioglycamic acid, Iophenoic acid, Iotroxic acid, Mefenamic acid, Naproxen, Nedocromil, Repaglinide, Salazosulfapyridine, Salicylic Acid, Salsalate, and Sarpogrelate.

Flavonoids, sometimes called bioflavonoids, are 3-ring phenolic compounds consisting of a double ring attached by a single bond to a third ring. Examples include flavonoids, flavanones, flavones, flavanols, anthocyanidins, proanthocyanidins, procyanidolic oligomers (PCO), catechins, biflavans, polyphenols, rutin, rutinosides, hydroxyethylrutosides (HER), hesperidin, quercetin, quercetrin, polyphenols, catechin, epicatechin, epicatechin gallate, epigallocatechin gallate, and leucoanthocyanins. Flavonoids include the water-soluble pigments, such as anthocyanins, that are found in cell vacuoles. Flavonols are colorless or yellow flavonoids found in leaves and many flowers.

A therapeutic dose of bioflavonoids is helpful for conditions related to Chronic Venous Insufficiency (CVI). Some examples are: thrombophlebitis, thrombosis, varicose veins, leg ulcers, spider veins, hemorrhoids, chronic nosebleeds, prolonged menstrual bleeding. Even eye problems like macular degeneration and diabetic retinopathy have been helped with bioflavonoids. Along with the anti-inflammatory effects, bioflavonoids can be very helpful for tendonitis, arthritis, rheumatoid arthritis, joint injury, fibromyalgia, cellulite, and gout. Bioflavonoids, specifically proanthcyanidins, are found in grape seed extract. The proanthcyanidins appear to enhance the activity of vitiamin C. The bioflavonoids in grape seed extract may also reduce the painful inflammation of swollen joints and prevent the oxidation of cholesterol in arteries that leads to plaque in the arterial walls.

Isoflavones exert a broad spectrum of biological activities. Besides antioxidant and estrogenic activities, isoflavones protect against several chronic diseases. Results of epidemiological studies indicate that consumption of soybean isoflavones lowers the incidence of breast, prostate, urinary tract and colon cancers. They also provide protection against coronary heart diseases and osteoporosis. Examples of isoflavones include are glycitein (isoflavone), daidzein, prunetin, biochanin A, orobol, santal, pratensein, formononetin, genistein, glycitein, and the glucosides, β-glycosides and other derivatives of the aforementioned isoflavones.

Further examples of biologically active compounds with hydroxyl, carboxyl and/or amino groups useful in the present invention may be found in the following texts, the disclosures of which are hereby incorporated herein by reference, in their entireties.

a. Shahidi, Ferriodoon and Marian Naczk, *Phenolics in Food and Nutriceuticals*, Boca Raton, Fla.: CRC Press, 2003.
b. Kleemann, A. et al, *Pharmaceutical Substances*, 4th Edition, Thieme (2000).
c. *Phenolic Compounds in Food and Their Effects on Health II; Antioxidants and Cancer Prevention*, ACS Symposium Series No. 507, Washington, D.C.: ACS, 1992.
d. *Food Phytochemicals for Cancer Prevention I*, ACS Symposium Series N. 546, Washington, D.C.: ACS, 1994.
e. *ROMPP Encyclopedia Natural Products*, New York: Thieme, 2000.
f. *The Merck Index*, 14$^{th}$ edition, John Wiley & Sons, 2007.
g. *A Single Source for Flavonoids and Coumarins* (2005-2006), INDOFINE Chemical Company, Inc. 2006.

The present invention provides novel biodegradable polyesters of formula III or a pharmaceutically acceptable salt thereof:

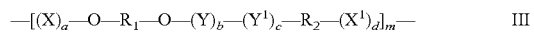

wherein the polyester is formed by condensation polymerization of monomers of formula I and II:

wherein:
m is an integer from about 5 to about 1000;
$R_1$ is the remaining portion of a biologically active compound;
$R_2$ is the remaining portion of a biologically active compound or non-biologically active compound;
$R_3$ and $R_4$ are independently selected from Cl, F, Br, and I;
X and $X^1$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;
Y and $Y^1$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
each y and z is independently an integer from about 2 to about 24; and
each a, b, c, and d is independently an integer from about 1 to about 6.

The present invention also provides novel biodegradable polyesters of formula VI or a pharmaceutically acceptable salt thereof:

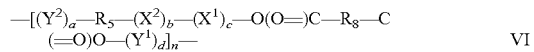

wherein the polyester is formed by condensation polymerization of monomers of formula IV and V:

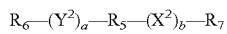  IV

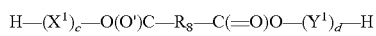  V wherein:
n is an integer from about 5 to about 1000;
$R_5$ is the remaining portion of a biologically active compound;
$R_6$ and $R_7$ are independently selected from Cl, F, Br, and I;
$R_8$ is the remaining portion of a biologically active compound or non-biologically active compound;
$X^1$ and $X^2$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;
$Y^1$ and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
each y and z is independently an integer from about 2 to about 24; and
each a, b, c, and d is independently an integer from about 1 to about 6.

The present invention also provides novel biodegradable polyamide esters of formula VIII or a pharmaceutically acceptable salt thereof:

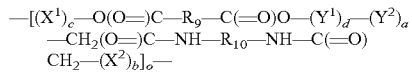  VIII wherein the polyamide ester is formed by condensation polymerization of monomers of formula Va and VII:

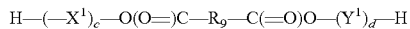  Va

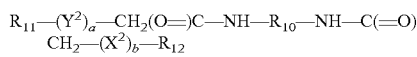  VII wherein:
o is an integer from about 5 to about 1000;
$R_9$ is the remaining portion of a biologically active compound;
$R_{10}$ is the remaining portion of a biologically active compound or non-biologically active compound;
$R_{11}$ and $R_{12}$ are independently selected from Cl, F, Br, and I;
$X^1$ and $X^2$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;
$Y^1$ and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
each y and z is independently an integer from about 2 to about 24; and
each a, b, c, and d is independently an integer from about 1 to about 6.

The present invention also provides novel biodegradable polyamide esters of formula IX or a pharmaceutically acceptable salt thereof:

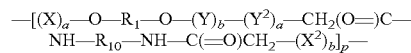  IX wherein the polyamide ester is formed by condensation polymerization of monomers of formula I and VII:

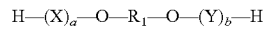  I

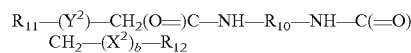  VII wherein:
p is an integer from about 5 to about 1000;
$R_1$ is the remaining portion of a biologically active compound;
$R_{10}$ is the remaining portion of a biologically active compound or non-biologically active compound;
$R_{11}$ and $R_{12}$ are independently selected from Cl, F, Br, and I;
X and $X^2$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—; and,
Y and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
each y and z is independently an integer from about 2 to about 24; and
each a, b, c, and d is independently an integer from about 1 to about 6.

The present invention also provides novel biodegradable polyesters of formula XI or a pharmaceutically acceptable salt thereof:

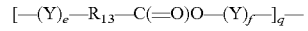  XI wherein the polyester is formed by self condensation polymerization of a monomer of formula X:

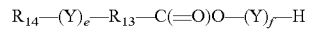  X wherein:
q is an integer from about 5 to about 1000;
$R_{13}$ is the remaining portion of a biologically active compound;
$R_{14}$ is selected from Cl, F, Br, and I;
Y is independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
each e is independently an integer from about 1 to about 6; and
each f is independently an integer from about 0 to about 6.

The present invention also provides novel biodegradable monomers of formulas I, II, IV, V, Va, VII, or X, as defined herein.

The groups represented by X, $X^1$, $X^2$, Y, $Y^1$, and $Y^2$ are attached in the monomers, oligomers and polymers of the present invention as shown. Their left hand sides are attached to the variable or H shown in the corresponding formula to be on the left of the X, $X^1$, $X^2$, Y, $Y^1$, or $Y^2$ group and on their right hand sides to the variable or H shown in the corresponding formula to be on the right of the X, $X^1$, $X^2$, Y, $Y^1$, or $Y^2$ group.

As set forth in formulas I, II, III, IV, V, VI, VII, VIII, IX, X and XI above, each of a, b, c, d and e is independently an integer from about 1 to about 6 (and all combinations and subcombinations of integer ranges and specific integers therein).

In certain preferred embodiments of the present invention, a is the integer 1, 2, or 3.

In other embodiments of the present invention, b is the integer 1 or 2.

In still other embodiments of the present invention, c is the integer 1.

As set forth in formulas X and XI above, f is independently an integer from about 0 to about 6 (and all combinations and subcombinations of integer ranges and specific integers therein).

As set forth in formulas III, VI, VIII and IX above, each of m, n, o, p and q is independently an integer of from about 5 to about 1000 (and all combinations and subcombinations of integer ranges and specific integers therein). In some preferred embodiments of the present invention, each of m, n, o, p and q is independently the integer 5, 10, 20, 30, 40, 50, 60, 70, 80, 90, 100, 200, 300, 400, 500, 600, 700, or 800, or an integer of from 900 to 1,000.

In the above groups X, $X^1$, $X^2$, Y, $Y^1$ and $Y^2$, each y and z is independently an integer from about 2 to about 24 (and all combinations and subcombinations of integer ranges and specific integers therein). In certain preferred embodiments, each y and z is independently selected from the integers 2, 3, 4, 5, 6, 7, 8, 9, 10, 11, 12, 13, 14, 15, 16, 17, 18, 19, 20, 21, 22, 23, or 24.

In certain preferred embodiments of the present invention, X, $X^1$, and $X^2$ are independently at each occurrence selected from: —OC(=O)CH$_2$—; —OC(=O)CH(CH$_3$)—; —OC(=O)CH$_2$CH$_2$OCH$_2$—; and —OC(=O)CH$_2$CH$_2$CH$_2$CH$_2$CH$_2$—; more preferably selected from —OC(=O)CH$_2$— and —OC(=O)CH(CH$_3$)—.

In other preferred embodiments of the present invention, Y, $Y^1$, and $Y^2$ are independently at each occurrence selected from: —CH$_2$C(=O)O—; —CH(CH$_3$)C(=O)O—; —CH$_2$CH$_2$OCH$_2$C(=O)O—; and, —CH$_2$CH$_2$CH$_2$CH$_2$CH$_2$C(=O)O—; more preferably selected from —CH$_2$C(=O)O— and —CH(CH$_3$)C(=O)O—.

In certain embodiments of the present invention the biologically active or non-biologically active compound has one or more amino groups which are incorporated into the backbone of the polymer of the invention. Whenever a Y, $Y^1$, or $Y^2$ is directly attached through its carboxyl terminus (the CO$_2$ side of the Y, $Y^1$, or $Y^2$) to an amino group of the biologically active or non-biologically active compound, the resulting bond is an amide bond. For example, when Y is CH$_2$—C(=O)O— and the biologically active compound to which it is attached is para-aminobenzoic acid, the resultant moiety is para-CH$_2$—C(=O)NH-benzoic acid. Similarly, whenever an X, $X^1$, or $X^2$ is directly attached through its carboxyl terminus (the CO$_2$ side of the X, $X^1$, or $X^2$) to an amino group of the biologically active or non-biologically active compound, the resulting bond is an amide bond.

The polymers of the present invention are designed such that the backbones comprise at least about one or at least about two functional groups that will preferably yield a biologically active form of a biologically active compound upon hydrolysis of the polymer.

The present invention also provides novel therapeutic methods for producing effects or treating diseases by administering to a patient in need thereof a therapeutically effective amount of at least one polymer of the present invention. Examples of effects and diseases include an analgesic effect, cancer, an anti-inflammatory effect, an anti-bacterial effect, an anti-fungal effect, an immunosuppressive effect, an anti-thrombotic effect, psoriasis, inflammatory bowel disease, skin cancer, brain tumor, an anti-infective effect, and pain.

In other preferred embodiments of monomers and/or oligomers of the present invention, $R^3$, $R^4$, $R^6$, $R^7$, $R^{11}$, and $R^{12}$ are each independently Cl, Br, or I, more preferably Cl or Br, with Cl being even more preferred.

Examples of biologically active compounds that may be included in the monomers, oligomers or polymers of the present invention include phenolic compounds such as phenols, naphthols, indoles, acetophenones, benzophenones, coumarins, furanocoumarins, alkaloids, catechins, chromones, chalcones, flavonoids or bioflavonoids, isoflavones, drugs containing phenolic groups, and natural products containing phenolic groups.

Examples of biologically active dihydroxy compounds that may be included in the monomers, oligomers or polymers of the present invention include Adrenalone, Alfuzosin, Alibendol, Amrubicin, Apomorphine, Bamethan, Benzquinamide, Bevantolol, Bifluranol, Bisacodyl, Brodimoprim, Bunazosin, Bupheniode, Carbidopa, Carbuterol, Cyclofenil, Cyclovalone, Daunorubicin, Dichlorophen, Dienestrol, Diethylstilbestrol, Dimestrol, Dithranol, Donepezil, Doxefazepam, Doxorubicin, Entacapone, Epinepheine, Epirubicin, Esomeprazole, Etamivan, Etamsylate, Etilefrine, Ezetimibe, Fenticlor, Fluorescein, Folescutol, Formoterol, Gefitinib, Hexestrol, Hexylresorcinol, Hydroxyethyl salicylate, Ifenprodil, Isoetarine, Isoxsuprine, Itopride. HCl, Khellin, Labetalol, Mitoxantrone, Morclofone, Moxaverine, Normolaxol, Omeprazole, Oxilofrine, Oxepertine, Phenacaine, Phenolphthalein, Prazosin, Tolcapone, Vesnarinone, and Vetradutine.

Examples of biologically active diamino compound that may be included in the monomers, oligomers or polymers of the present invention include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, and D-Norpseudoephedrine.

Examples of biologically active hydroxy/amino compounds that may be included in the monomers, oligomers or polymers of the present invention include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudoephedrine, and paracetamol.

Examples of biologically active dicarboxylic acid compounds that may be included in the monomers, oligomers or polymers of the present invention include Adipiodone, Cromoglicic acid, Eprosartan, Iocarmic acid, Iodoxamic acid, Ioglycamic acid, Iotroxic acid, Nedocromil.

Examples of biologically active hydroxy/carboxylic acid compounds that may be included in the monomers, oligomers or polymers of the present invention include Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, and Sarpogrelate.

Examples of biologically active hydroxyl-acids that may be included in the monomers, oligomers or polymers of the present invention include 4-hydroxycinnamic acid, caffeic acid, chlorogenic acid, ferulic acid, sinapic acid, vanillic acid, Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, and Sarpogrelate.

Examples of biologically active amino/carboxylic acid compounds that may be included in the monomers, oligomers or polymers of the present invention include Aceclofenac, Acediasulfone, Alminoprofen, AmLexanox, Anileridine, Baccofen, Balsalazide sodium, Benzocaine, Bumetanide, Carprofen, Carzenide, Diclofenac, Flufenamic acid, Furosemide, Iobenzamic acid, Iocetamic acid, and Mefenamic acid.

Examples of biologically active diamino compounds that may be included in the monomers, oligomers or polymers of the present invention include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudoephedrine, amino acids (L-lysine), and natural products.

Non-biologically active diol compounds include saturated and unsaturated, substituted and unsubstituted alkyl, aryl and alkylaryl groups having 2, 3, 4, 5, 6, 7, 8, 9, 10, 11, 12, 13, 14, 15, 16, 17, or 18 carbon atoms. Alternatively, polyalkylene oxides having weight average molecular weights of from about 500 to about 5,000 may be used as a diol (i.e., a polydiol). Suitable diols or polydiols for use in the present invention are diol or diol repeating units with up to about 8 carbon atoms. Examples of suitable diols include 1,2-ethanediol (ethylene glycol); 1,2-propanediol (propylene glycol); 1,3-propanediol; 1,4-butanediol; 1,5-pentanediol; 1,3-cyclopentanediol; 1,6-hexanediol; 1,4-cyclohexanediol; 1,8-octanediol; and, combinations thereof. Examples of polydiols include polyethylene glycol and polypropylene glycol with weight average molecular weights of from about 500 to about 5000.

Examples of non-biologically active dicarboxylic compounds useful in the present invention include saturated and unsaturated, substituted and unsubstituted alkyl, aryl and alkylaryl groups having 1, 2, 3, 4, 5, 6, 7, 8, 9, 10, 11, 12, 13, 14, 15, 16, 17, or 18 carbon atoms. Alternatively, non biologically active symmetrical and non symmetrical dicarboxylic acids as shown below can also be used in the present invention;

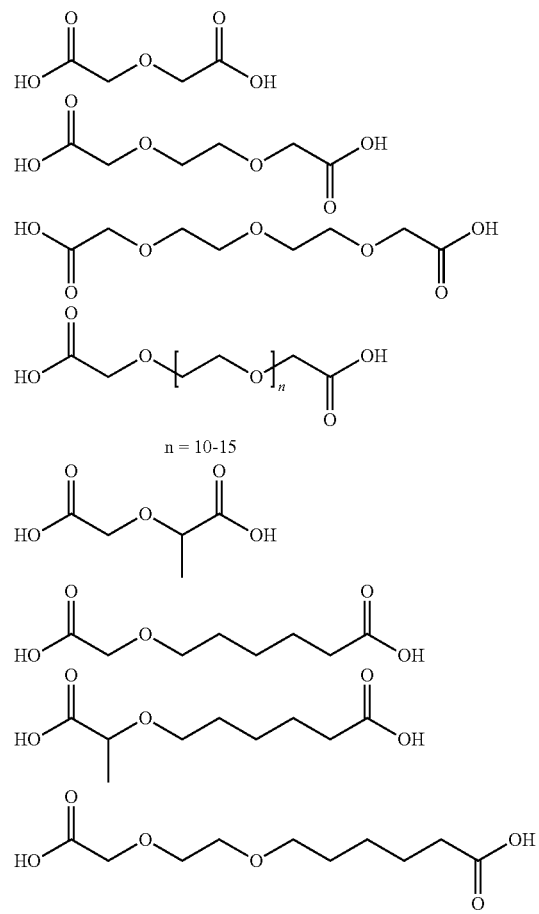

$n = 10-15$

Examples of non-biologically active diamino compounds useful in the present invention include saturated and unsaturated, substituted and unsubstituted alkyl, aryl and alkylaryl groups having 2, 3, 4, 5, 6, 7, 8, 9, 10, 11, 12, 13, 14, 15, 16, 17, or 18 carbon atoms. Alternatively, polyalkylene oxides that are diamines with weight average molecular weights from about 500 to about 5,000 may be used. Alternatively, non biologically active symmetrical and non symmetrical diamines as shown below can also be used in the present invention;

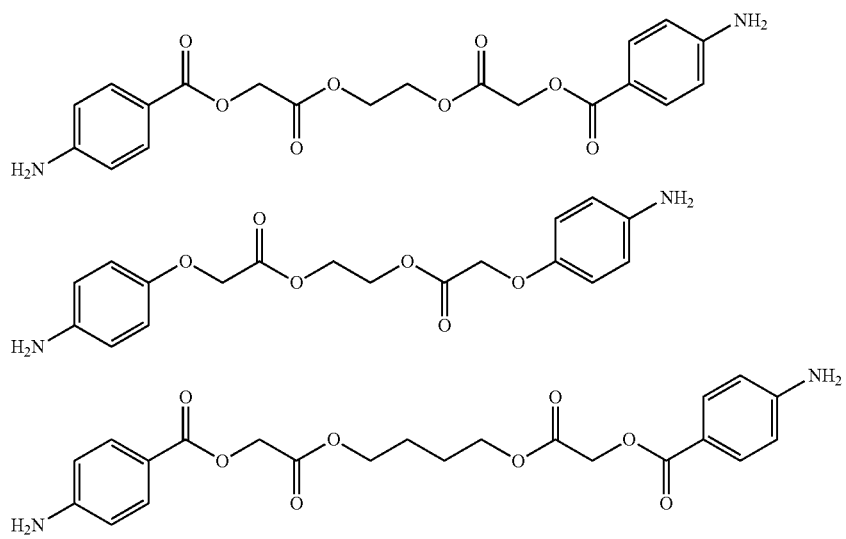

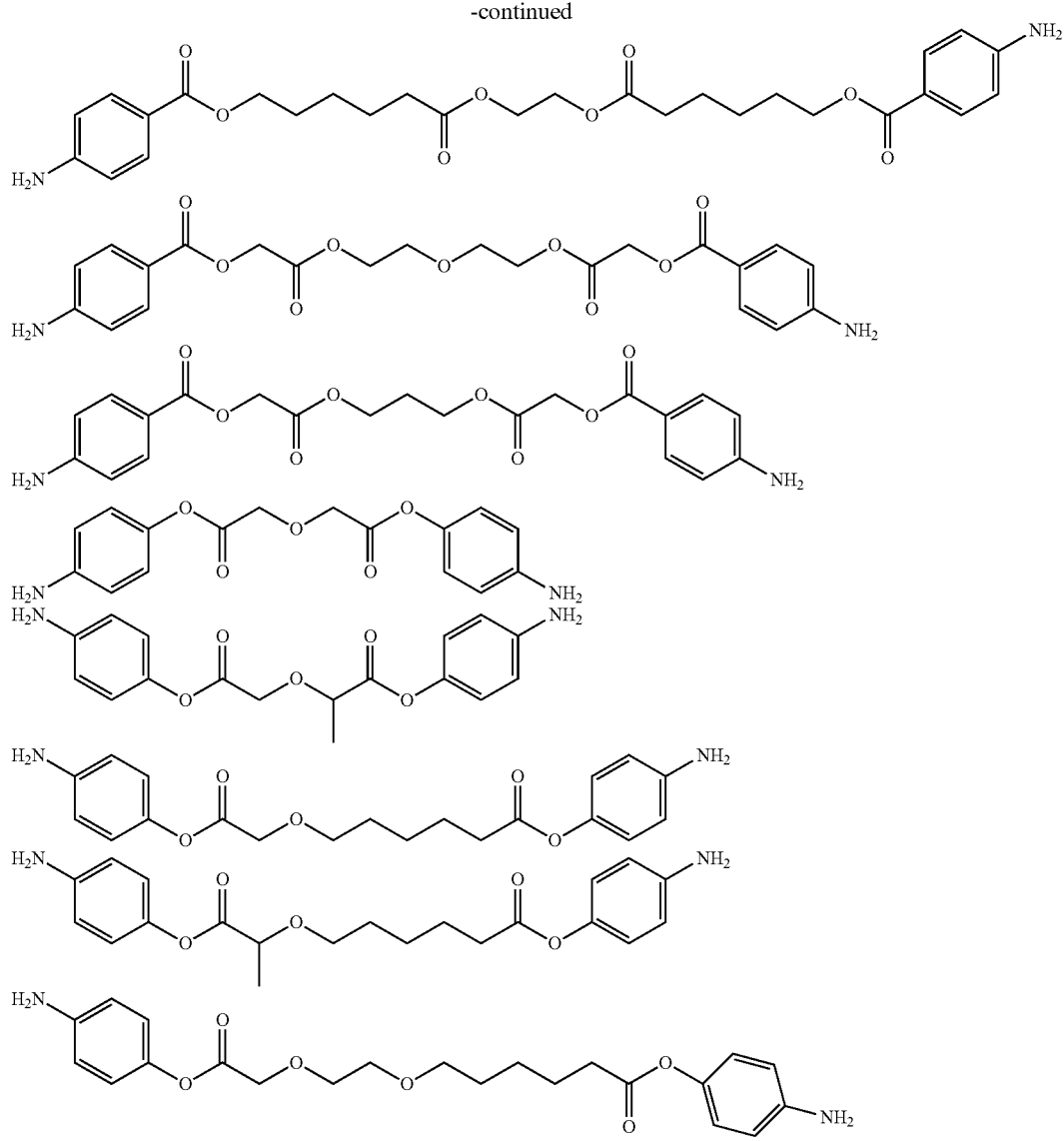

-continued

The definitions and examples provided in this application are not intended to be limiting, unless specifically stated.

"Patient" as used herein refers to any animal in need or medical care or other treatment that employs the polymers of the invention. The term animal includes for example, mammals, especially those warm blooded mammals that are typically under medical care (e.g., humans and domesticated animals). Examples of mammals include feline, canine, equine, bovine, and human, more preferably human.

The monomers and polymers described herein may be useful in medical applications, including as drug delivery devices and other medical devices. The terms "medical applications" and "medical devices", as used herein, encompass medical and biomedical applications and include all types of applications involved in the practice of medicine that would benefit from a material that may decompose harmlessly within about a known or desired period of time. Examples include medical and surgical devices, which include drug delivery systems (e.g., a site-specific or systemic drug delivery systems or matrices), tissue engineering (e.g., tissue scaffold), stent coatings, stents, porous devices, implantable medical devices, molded articles (e.g., vascular grafts, stents, bone plates, sutures, implantable sensors, and barriers for surgical adhesion prevention), wound closure devices (e.g., surgical clips, staples, and sutures), coatings (e.g., for endoscopic instruments, sutures, stents, and needles), fibers or filaments (which may be attached to surgical needles or fabricated into materials including sutures or ligatures, multifilament yarn, sponges, gauze, tubes, and sheets for typing up and supporting damaged surface abrasions), rods, films (e.g., adhesion prevention barriers), knitted products, foodstuffs, nutritional supplements, nutraceuticals, cosmetics, pharmaceuticals, biodegradable chewing gums, flavors, enhanced drugs, drug intermediates, cancer preventing agents, antioxidants, controlled release preparations, and solvents for drugs. Examples of knitted products, woven or non-woven, and molded products include: burn dressings; hernia patches; medicated dressings; facial substitutes; gauze, fabric, sheet, felt, or sponge for liver hemostasis; gauze bandages; arterial graft or substitutes; bandages for skin surfaces; suture knot clip; orthopedic pins, clamps, screws, and plates; clips (e.g., for vena cava); staples; hooks, buttons, and snaps; bone substitutes (e.g., mandible prosthesis); intrauterine devices (e.g., spermicidal devices); draining or testing tubes or capillaries; surgical instruments; vascular implants or supports; vertebral discs; extracorporeal tubing for kidney and heart-lung machines; and, artificial skin.

The rate of hydrolysis of the materials of the present invention will depend upon a number of factors, including the functionalization used and the number of functionalizations present on the at least difunctionalized aromatic (e.g., from about 1 to about 6). For example, glycolic acid modified aromatics should generally hydrolyze more quickly than aromatics modified with dioxanone, whereas lactic acid and caprolactone modified aromatics should generally hydrolyze over a longer period of time as compared to glycolic acid and dioxanone modified aromatics. Furthermore, it is expected that the rate of hydrolysis will increase as the number of functional groups is increased. Thus, desired time ranges for hydrolysis and therefore release of biologically active agents may be obtained by altering the number and type of functionalization used to functionalize the aromatics.

Polymers of the present invention preferably have weight-average molecular weights above about 10,000 including, for example, about 20,000 or above, about 30,000 or above, about 40,000 or above, about 50,000 or above, about 60,000 or above, about 70,000 or above, about 80,000 or above, including about 90,000 to about 100,000 daltons, calculated from gel permeation chromatography (GPC) relative to polystyrene standards in tetrahydrofuran (THF) without further correction.

The polymers of the present invention may preferably be processed by known methods commonly employed in the field of synthetic polymers to provide a variety of useful articles with valuable physical and chemical properties. The useful articles may be shaped by conventional polymer-forming techniques such as extrusion, compression molding, injection molding, solvent casting, and wet spinning. Shaped articles prepared from the polymers may be useful, for example, as degradable devices for medical implant applications.

The present invention also relates to compositions, comprising: at least one functionalized aromatic, wherein the composition is suitable for use as at least one of the following: (a) a solvent for drugs; (b) a nutritional compound; (c) a cosmetic: and, (d) a pharmaceutical. Each of the compositions may further comprise an additional component suitable for such compositions. For example, when the composition is suitable for use as a cosmetic it may further comprise one or more cosmetic ingredients. Also, when the composition is suitable for use as a pharmaceutical it may further comprise one or more pharmaceutically acceptable excipients. In addition, each of the compositions may comprise a difunctionalized aromatic derived from a aromatic having a property useful to that type of composition. For example, the starting aromatic may be (a) a nutritional supplement or a food intermediary; (b) an anticancer agent; (c) an antimicrobial agent; (d) an anti-inflammatory agent; (e) a pain-reducer; and, (f) an antioxidant agent. Also, the compositions may further comprise one of agents (a)-(f).

The compositions of the present invention may be suitable for administration via a route selected from oral, enteral, parenteral, topical, transdermal, ocular, vitreal, rectal, nasal, pulmonary, and vaginal.

The implantable medical devices of the present invention comprise at least one absorbable polymer of the present invention. For example, a polymer of the present invention may be combined with a quantity of a biologically active compound sufficient to be therapeutically effective as a site-specific or systemic drug delivery system (see Gutowska et al., J. Biomater. Res., 29, 811-21 (1995) and Hoffman, J. Controlled Release, 6, 297-305 (1987), the disclosures of which are hereby incorporated herein by reference, in their entirety). Another example of the present invention is a method for site-specific or systemic drug delivery by implanting in the body of a patient in need thereof an implantable drug delivery device comprising a therapeutically effective amount of a biologically active compound in combination with at least one absorbable polymer of the present invention.

In another example, at least one polymer of the present invention is formed into a porous device (see Mikos et al., Biomaterials, 14, 323-329 (1993) or Schugens et al., J. Biomed. Mater. Res., 30, 449-462 (1996)) to allow for the attachment and growth of cells (see Bulletin of the Material Research Society, Special Issue on Tissue Engineering (Guest Editor: Joachim Kohn), 21(11), 22-26 (1996)). The disclosures of the foregoing publications are hereby incorporated herein by reference, in their entireties. Thus, the present invention provides a tissue scaffold comprising a porous structure for the attachment and proliferation of cells either in vitro or in vivo formed from at least one absorbable polymer of the present invention The present invention also relates to an article (e.g., an implantable medical device), comprising a metal or polymeric substrate having thereon a coating, wherein the coating comprises at least one polymer of the present invention.

The present invention also relates to a molded article prepared from at least one polymer of the present invention.

Controlled release mechanisms are known in the art. See, for example, Langer, R., Science 249: 1527-1533 (1990); WO 02/09768; WO 02/09767; WO 01/41753; WO 99/12990, the disclosures of which are hereby incorporation herein by reference, in their entireties. Any and all controlled release mechanisms and formulations may be employed in practicing the invention, provided it allows for the controlled release of the biologically active compounds at, or near, the site of interest.

Polymeric drug delivery systems comprising the polymers of the invention may be readily processed into pastes or solvent cast to yield films, coatings, nanoparticles e.g. nanospheres, microparticles e.g. microspheres and fibers with different geometric shapes for design of various medical devices, and may also be processed by compression molding and extrusion. In one embodiment, a polymer or polymers may be coated onto or applied onto a medical device, such as, e.g., by forming the polymer or polymers into a covering. In another embodiment, the polymer or polymers may be formed into a medical device, such as, e.g., an implant. In one embodiment of the present invention, a polymer comprising a functional group or agent may used to form a covering, such as, e.g., a coating or a sheath, that partially or completely covers and/or surrounds a medical device. Such a covering may cover a portion of the medical device or it may completely cover a medical device. The covering may be divided into separate portions or several smaller coverings may be present on the medical device. In another embodiment of the invention, a polymer may surround the medical device, or a portion thereof, and may have the form of a coating, a layer, a film, and combinations thereof. The polymer may be in the form of a solid or a semi-solid, such as a gel, sheath, a wrap, a tube or a cuff covering all or a portion of the medical device. The polymer may be rigid, semi-rigid, or non-rigid. The coating of polymer may be, for example, about 100 nm, about 1 mm, about 1 mm, or about 1 cm thick, although some porous implants may benefit from longer lasting effects enabled by a coating that completely fills the interstices of the device with, in some cases, a thin coating on those surfaces proximal to bone or other tissue upon placement in the body. In one embodiment, the polymer coating may be comprised of microparticles, such as microspheres that may typically but not necessarily be less than about 10 microns in diameter. These microparticles may be applied to the surface of a medical device before placement in the body. A sterile liquid may be used to coat the device to adhere such microspheres for minutes to weeks to enable uncoated medical devices to benefit from the same or similar therapeutic benefits as coated devices.

A polymer, compound and/or composition of the invention may be applied or coated onto a medical implant by any means known in the art including, but not limited to, solvent methods such as, for example, dipping and spray-drying, and non-solvent methods such as chemical vapor deposition, extrusion coating, covalently grafting or dipping in molten polymer, compound and/or composition of the invention. The method of preparation may vary depending on the polymer, compound and composition and/or the medical implant. The medical implant may be formed from or coated with one or more layers of the same or different polymer, compound and/or composition of the invention. In another example, a polymer, compound and/or composition of the invention may be coated onto a medical implant in the shape of a membrane or tube for use in the treatment of injury or damage to the peripheral nervous system or a block of solid or foamed composition containing pathways drilled or otherwise formed to encouraged nerve growth or bone growth. In the above instances, bioerosion of the disc, membrane, tube or block would yield or generate an agent included within the polymer or composition. The polymer may be formed into a device by any means known in the art including, but not limited to, molding e.g. compression or blow molding, and extrusion. The medical device may be formed from one or more of the same or different polymer, compound and/or composition of the invention. A polymer, compound and/or composition of the invention may be formed, that is, physically configured, into various shapes, geometries, structures and configurations including, but not limited to, a film, fiber, rod, coil, corkscrew, hook, cone, pellet, tablet, tube e.g. smooth or fluted, disc, membrane, microparticle, nanoparticle, "biobullet" i.e. bullet shaped, seed i.e. bullet shaped or targeted seeds, as well as those described in the above identified products, patents and articles, including in some cases forming medical implants that have the same, similar or completely different functional characteristics compared to those functional characteristics of the medical devices described in the above identified products, patents and articles. The above-mentioned shapes, geometries, structures and configurations may contain additional features that will further enhance the desired application or use. For example, a polymer, compound and/or composition of the invention in the form of a rod, coil, or cone may have barbs that spring out upon insertion from a needle or cannula or when warmed to body temperature to reduce movement and/or expulsion. The shape, geometry, structure or configuration of a device, such as a medical implant, will vary depending upon the use of the device. For example, for treatment of a spinal cord injury or concussion to the brain, a polymer, compound and/or composition of the invention may be formed into a medical implant in the shape of a disc for placement under the dura or dura mater, or a solution, suspension, emulsion, cream, gel, ointment, or other adhesive formulation form for covering the spine, dura or other surgically exposed areas, film, sprayed or coated formulation. In another example, a polymer, compound and/or composition of the invention may be formed into a medical implant in the shape of a membrane or tube for use in the treatment of injury or damage to the peripheral nervous system or a block of solid or foamed composition containing pathways drilled or otherwise formed to encourage nerve growth or bone growth. In another example, in the treatment of cancer, a polymer, compound and/or composition of the invention may be formed into a medical implant in the shape of a pellet, microparticle e.g. microsphere, nanoparticle e.g. nanosphere, rod, membrane, pin, cuff, disc, bullet, hook, rod or cone, with or without barbs, for insertion in a bone, joint, tumor excision site or other structures, or for insertion within the same and other structures. In the above instances, bioerosion of the medical implant would yield or generate an agent.

The present invention also relates to a controlled drug delivery system comprising at least one polymer of the present invention physically admixed with a biologically or pharmacologically active agent. For example, the controlled drug delivery system can comprise a biologically or pharmacologically active agent coated with at least one polymer of the present invention.

The present invention also relates to a controlled drug delivery system comprising a biologically or pharmacologically active agent physically embedded or dispersed into a polymeric matrix formed from at least one polymer of the present invention.

The present invention also relates to a tissue scaffold having a porous structure for the attachment and proliferation of cells, either in vitro or in vivo, formed from one least one polymer of the present invention.

The present invention also relates to a composition comprising at least one polymer of the present invention, which has been further polymerized with at least one lactone monomer selected from glycolide, lactide, p-dioxanone, trimethylene carbonate, ether lactones, morpholinediones, and caprolactone.

The present invention also relates to an implantable biomedical device comprising at least one polymer that has been further polymerized with at least one lactone monomer.

The present invention also relates to a biodegradable chewing gum composition comprising an effective amount of at least one polymer that has been further polymerized with at least on lactone monomer.

The present invention also relates to an article (e.g., an implantable medical device) comprising a metal or polymeric substrate and having thereon a coating, wherein said coating comprises at least one polymer that has been further polymerized with at least one lactone monomer.

The present invention also relates to a molded article prepared from at least one polymer that has been further polymerized with at least one lactone monomer.

The present invention also relates to a monofilament or multifilament prepared from at least one polymer that has been further polymerized with at least one lactone monomer.

The present invention also relates to a controlled drug delivery system comprising at least one polymer that has been further polymerized with at least one lactone monomer, which has been physically admixed with a biologically or pharmacologically active agent.

The present invention also relates to a controlled drug delivery system comprising a biologically or pharmacologically active agent physically embedded or dispersed into a polymeric matrix formed from at least one polymer that has been further polymerized with at least one lactone monomer.

The present invention also relates to a tissue scaffold having a porous structure for the attachment and proliferation of cells, either in vitro or in vivo, formed from at least one polymer that has been further polymerized with at least one lactone monomer.

The present invention also relates to low molecular weight polymers or oligomers of the compounds of the present invention that are further reacted to form reactive end groups (e.g., isocyanates, expoxides, acrylates and the like). Low-molecular weight polymers or oligomers as used herein means a polymer having a number average molecular weight of about 500 to about 20,000 (and all combinations and sub-combinations of ranges of number average molecular weights and specific molecular weights therein), with about 500 to about 10,000 being preferred. For example, some of the compounds of the present invention may behave chemically like diols. They may therefore be reacted with dicarboxylic acids to form polyesters, which are usually hydroxyterminated. These hydroxyterminated oligomers may be further reacted to form, for example, isocyanates, epoxides and acrylates. Similarly the compounds of the present invention may be reacted with isocyanates to make urethanes. Thus, the present invention also includes compositions comprising at least one polymer of the present invention, which has been further reacted to form reactive end groups.

The present invention also relates to polymers made from compounds of the present invention that have been sterilized, for example, by cobalt-60 radiation, electron beam radiation, and/or ethylene oxide.

"Bioabsorbable" or "absorbable" as used herein means that the material readily reacts or enzymatically degrades upon exposure to bodily tissue for a relatively short period of time, thereby experiencing a significant weight loss in that short period of time. Complete bioabsorption/absorption should take place within about twenty four months, although it may be complete within about nine months or within about six months. In this manner, the polymers of the present invention may be fabricated into medical and surgical devices, which may be useful for a vast array of applications requiring complete absorption within a relatively short time period.

The biological properties of the bioabsorbable polymers of the present invention used to form a device or part thereof, as measured by its absorption rate and its breaking strength retention in vivo (BSR), may be varied to suit the needs of the particular application for which the fabricated medical device or component is intended. This can be conveniently accomplished by varying the ratio of components of the polymer chosen.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat the desired indication.

"Alkyl" includes both branched and unbranched saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, s-pentyl, and n-hexyl.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, and tetrahydronaphthyl.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl include acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Polymers of the present invention may be made in the form of random copolymers or block copolymers. A coupling agent may also be added to the polymers of the present invention. A coupling agent is a reagent that has a least two functional groups that are capable of covalently bonding to two different monomers. Examples of coupling agents include trifunctional or tetrafunctional polyols, oxycarboxylic acids, and polybasic carboxylic acids (or acid anhydrides thereof). Other coupling agents include the difunctional groups (e.g., diols, diacids, diamines, and hydroxy-acids) previously discussed. The addition of the coupling agents causes the branching of long chains, which can impart desirable properties in the molten state to the pre-polymer. Examples of polyfunctional coupling agents include trimethylol propane, glycerin, pentaerythritol, malic acid, citric acid, tartaric acid, trimesic acid, propane tricarboxylic acid, cyclopentane tetracarboxylic anhydride, and combinations thereof.

A "pre-polymer" is a low-molecular weight polymer, as previously defined, that have reactive end groups (e.g., hydroxy groups) that can be further reactive with, for example, the lactone monomers.

The amount of coupling agent to be added before gelation occurs is a function of the type of coupling agent used and the polymerization conditions of the polymer or molecular weight of the pre-polymer to which it is added. Generally in the range of from about 0.1 to about 10 mole percent of a trifunctional or a tetrafunctional coupling agent may be added based on the moles of polymers present or anticipated from the synthesis.

The polymerization of a polyester of the present invention can be performed under solution polymerization conditions in the presence of an triethylamine catalyst at room temperature to below about 80° C., preferably at about room temperatures. The exact reaction conditions chosen will depend on numerous factors, including the properties of the polymer desired, the viscosity of the reaction mixture, and the glass transition temperature and softening temperature of the polymer. Desired reaction conditions of temperature, time and pressure can be readily determined by assessing these and other factors. Generally, the reaction mixture will be maintained at about room temperature for many hours. The polymerization reaction can be allowed to proceed at this temperature until the desired molecular weight and percent conversion is achieved for the copolymer, which will typically take about 15 minutes to about 40 hours. Increasing the reaction temperature generally decreases the reaction time needed to achieve a particular molecular weight.

Polymerization conditions for the preparation of other types of polymers of the present invention (e.g., polyamides) are described in the literature. Those skilled in the art will recognize that the polymers described herein can be made from known procedures, once armed with the teachings of the present disclosure.

Copolymers of the absorbable polymers of the present invention can be prepared by preparing a pre-polymer in solution, isolating, purifying and drying, then adding at least one lactone monomer or lactone pre-polymer. The mixture could then be subjected to the desired conditions of temperature and time to copolymerize the pre-polymer with the lactone monomers.

A lactone pre-polymer is a pre-polymer formed by ring opening polymerization with a known initiator (e.g., ethylene glycol, diethylene glycol, glycerol, or other diols or triols).

The molecular weight of the pre-polymer as well as its composition can be varied depending on the desired characteristic, which the pre-polymer is to impart to the copolymer. For example, the pre-polymers of the present invention, from which the copolymer is prepared, generally have a molecular weight that provides an inherent viscosity between about 0.2 to about 2.0 deciliters per gram (dl/g) as measured in a 0.1 g/dl solution of hexafluoroisopropanol at 25° C. Those skilled in the art will recognize that the pre-polymers described herein can also be made from mixtures of more than one diol or dicarboxylic acid.

One of the beneficial properties of the polyesters of the present invention is that the ester linkages are hydrolytically unstable, and therefore the polymer is bioabsorbable because it readily breaks down into small segments when exposed to moist bodily tissue. In this regard, while it is envisioned that co-reactants could be incorporated into the reaction mixture of the dicarboxylic acid and the diol for the formation of the polyester pre-polymer, it is preferable that the reaction mixture does not contain a concentration of any co-reactant which would render the subsequently prepared polymer non-absorbable. The reaction mixture can be substantially free of any such co-reactants if the presence thereof results in a non-absorbable polymer.

The polymers of the present invention can be melt processed by numerous methods to prepare a vast array of useful devices. These polymers can be injection or compression molded to make implantable medical and surgical devices, especially wound closure devices.

Alternatively, the polymers can be extruded to prepare fibers. The filaments thus produced may be fabricated into sutures or ligatures, attached to surgical needles, packaged, and sterilized by known techniques. The polymers of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Examples include tubes, including branched tubes, for artery, vein, or intestinal repair, nerve splicing, tendon splicing, sheets for typing up and supporting damaged surface abrasions, particularly major abrasions, or areas where the skin and underlying tissues are damaged or surgically removed.

Additionally, the polymers can be molded to form films which, when sterilized, are useful as adhesion prevention barriers. Another alternative processing technique for the polymers of the present invention includes solvent casting, particularly for those applications where a drug delivery matrix is desired.

The polymers of the present invention can be used to coat a surface of a surgical article to enhance the lubricity of the coated surface. The polymer may be applied as a coating using conventional techniques. For example, the polymer may be solubilized in a dilute solution of a volatile organic solvent (e.g. acetone, methanol, ethyl acetate, or toluene), and then the article can be immersed in the solution to coat its surface. Once the surface is coated, the surgical article can be removed from the solution where it can be dried at an elevated temperature until the solvent and any residual reactants are removed.

For coating applications, the polymer should exhibit an inherent viscosity, as measured in a 0.1 gram per deciliter (g/dl) of hexafluoroisopropanol (HFIP), between about 0.05 to about 2.0 dl/g or about 0.10 to about 0.80 dl/g. If the inherent viscosity were less than about 0.05 dl/g, then the polymer may not have the integrity necessary for the preparation of films or coatings for the surfaces of various surgical and medical articles. On the other hand, it is possible to use polymers with an inherent viscosity greater than about 2.0 dl/g, though it may be difficult to do so.

Numerous surgical articles (including but not limited to endoscopic instruments) can be coated with the polymer of the present invention to improve the surface properties of the article. By way of example, specific surgical articles include surgical sutures, stents, and needles. More specifically the surgical article may be a suture, which may be attached to a needle. The suture may also be a synthetic absorbable suture. These sutures are derived, for example, from homopolymers and copolymers of lactone monomers such as glycolide, lactide, ε-caprolactone, 1,4-dioxanone, and trimethylene carbonate. The suture can be a braided multifilament suture composed of polyglycolide or poly(glycolide-co-lactide).

The amount of coating polymer to be applied on the surface of a braided suture can be readily determined empirically, and will depend on the particular copolymer and suture chosen. Ideally, the amount of coating copolymer applied to the surface of the suture may range from about 0.5 to about 30 percent of the weight of the coated suture or from about 1.0 to about 20 weight percent, or from about 1 to about 5 percent by weight. If the amount of coating on the suture were greater than about 30 weight percent, then it may increase the risk that the coating may flake off when the suture is passed through tissue Sutures coated with the polymers of the present invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the polymer of the present invention.

When the article of the present invention is a metal stent, the amount of coating applied to the surface of the article is an amount which creates a layer with a thickness ranging, for example, between about 2 to about 20 microns on the stent or about 4 to about 8 microns. If the amount of coating on the stent were such that the thickness of the coating layer was greater than about 20 microns, or if the thickness was less than about 2 microns, then the desired performance of the stent as it is passed through tissue may not be achieved.

When the article of the present invention is a surgical needle, the amount of coating applied to the surface of the article is an amount which creates a layer with a thickness ranging, for example, from about 2 to about 20 microns on the needle, preferably of about 4 to about 8 microns. While coatings outside this range may still be operable, the performance of the needle as it is passed through tissue may not be optimum.

The polymers of the present invention can also be used as a pharmaceutical carrier in a drug delivery matrix. To form this matrix the polymer can be mixed with a therapeutic agent to form the matrix. There are a variety of different therapeutic agents, which can be used in conjunction with the polymers of the invention. In general, therapeutic agents which may be administered via the pharmaceutical compositions of the invention include, antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered in any suitable dosage form including orally, parenterally, subcutaneously as an implant, vaginally, or as a suppository. Matrix formulations containing the polymers of the present invention may be formulated by mixing one or more therapeutic agents with the polymer. The therapeutic agent, may be present as a liquid, a finely divided solid, or any other appropriate physical form. Typically, but optionally, the matrix will include one or more additives, e.g., nontoxic auxiliary substances such as diluents, carriers, excipients, or stabilizers. Other suitable additives may be formulated with the polymers of the present invention and pharmaceutically active agent. If water is to be used, then it can be useful to add it just before administration.

The amount of therapeutic agent will be dependent upon the particular drug employed and medical condition being treated. Typically, the amount of drug represents about 0.001% to about 70%, about 0.001% to about 50%, or about 0.001% to about 20% by weight of the matrix.

The quantity and type of polymer incorporated into a composition (e.g., parenterally delivered composition) will vary depending on the release profile desired and the amount of drug employed. The product may contain blends of polymers of the present invention to provide the desired release profile or consistency to a given formulation.

The polymers of the present invention, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (e.g., over about 1 to about 2,000 hours or about 2 to about 800 hours) of effective amounts (e.g., about 0.0001 mg/kg/hour to about 10 mg/kg/hour) of the drug. This dosage form can be administered as is necessary depending on the subject being treated, the severity of the affliction, and the judgment of the prescribing physician.

Individual formulations of drugs and polymers of the present invention may be tested in appropriate in vitro and in vivo models to achieve the desired drug release profiles. For example, a drug could be formulated with a polymer of the present invention and orally administered to an animal. The drug release profile could then be monitored by appropriate means such as, by taking blood samples at specific times and assaying the samples for drug concentration. Following this or similar procedures, those skilled in the art will be able to formulate a variety of formulations.

The polymers of the present invention can have controllable hydrolysis profiles, improved bioavailability, improved efficacy and enhanced functionality. The difunctional compounds can readily polymerize into biodegradable polyesters, polyester amides, for example, useful for many applications, including biomedical applications, foodstuffs, nutritional supplements, cosmetics, medicaments, coatings and others readily apparent to one skilled in the art.

An aspect of this invention is to combine these molecules, such as glycolic acid, lactic acid, p-dioxanone, $\epsilon$-caprolactone, $-(CH_2)_yCOO-$, where y is one of the integers 2, 3, 4 and from 6 to 24, and $-(CH_2CH_2O)_zCH_2COO-$, where z is an integer from 2 to 24, with aromatic compound, to form a new chemical entity. Preferential examples of functionalization molecules are glycolic acid, lactic acid, p-dioxanone, and $\epsilon$-caprolactone. This functionalization enhances the native value of the aromatic compound by releasing the aromatic moiety by hydrolysis or degradation of the compound. The compound may degrade under controllable conditions in the environment, in the body of an animal, for example a mammal, including a human.

The glycolic acid moiety, lactic acid moiety, dioxanone moiety, caprolactone moiety, moieties of $-(CH_2)_yCOO-$ where y is one of the integers 2, 3, 4 and from 6 to 24, and moieties of $-(CH_2CH_2O)_zCH_2COO-$ where z is an integer from 2 to 24, have different hydrolysis or degradation rates and times over which they release the active aromatic moiety and thus do the difunctionalized aromatic acid made from them. The species used for functionalization supplies the release time or range dictated by the application. Glycolic acid based compounds hydrolyze faster than p-dioxanone based whereas lactic acid and caprolactone based compounds take much longer to hydrolyze than glycolic acid and p-dioxanone based compounds. This desired time range may be obtained by using a combination of difunctionalized aromatic compounds, that is, a blend of two or more functionalized compounds made from any two or more of the species glycolide, lactide, dioxanone and polydioxanone combined with one aromatic compound.

The array of difunctionalized compounds developed as an aspect of the invention, have a wide range of hydrolysis rates that are controllable. The specific moiety or combination of moieties used for functionalization yields a compound or mixture with specific hydrolysis ranges.

Bioactive Formulations

In other aspects of the present invention some polymers of the present invention can be further manufactured into formulations suitable for oral, rectal, parenteral (for example, subcutaneous, intramuscular, intradermal, or intravenous), transdermal, vitreal or topical administration. The most suitable route in any given case will depend on the nature and severity of the condition being treated and on the nature of the particular active compound that is being used. The formulations of a pharmaceutical composition are typically admixed with one or more pharmaceutically or veterinarially acceptable carriers and/or excipients as are well known in the art.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion.

Compositions of the present invention suitable for parenteral administration conveniently comprise sterile aqueous preparations of the active compounds, which preparations are preferably isotonic with the blood of the intended recipient.

Formulations suitable for rectal administration are preferably presented as unit dose suppositories.

Formulations suitable for ocular or vitreal administration may be presented as bioabsorbable coatings for implantable medical devices, injectables, liquids, gels or suspensions.

Formulations or compositions suitable for topical administration to the skin preferably take the form of an ointment, cream, lotion, paste, gel, spray, aerosol, or oil. Examples of carriers that conventionally used include Vaseline, lanoline, polyethylene glycols, alcohols, and combination of two or more thereof.

Formulations suitable for transdermal administration may be presented as discrete patches adapted to remain in intimate contact with the epidermis of the recipient for a prolonged period of time.

The active compounds may be provided in the form of foodstuffs or nutrition supplements, such as being added to, admixed into, coated, combined or otherwise added to a foodstuff. The term foodstuff is used in its widest possible sense and includes liquid formulations such as drinks including dairy products, biodegradable chewing gums, and other foods, such as health bars, desserts, etc. Food formulations containing compounds of the invention can be readily prepared according to standard practices.

Compounds of the formula used as medicaments or pharmaceuticals are typically administered in a manner and amount as is conventionally practiced. See, for example, Goodman and Gilman, The Pharmaceutical Basis of Therapeutics, current edition, the disclosures of which are hereby incorporated herein by reference, in their entireties.

Compounds of the present invention may have potent antioxidant activity and increased acidity of their aromatic component, as well as the improved biodegradation provided by the functionalization, and thus find wide application in pharmaceutical and veterinary uses, in cosmetics such as more effective skin creams to prevent skin ageing, in sun screens, in foods, health drinks, nutritional supplements, shampoos, and the like.

Dosages

Useful dosages of the polymers can be determined by comparing their in vitro activity, and in vivo activity of the therapeutic agent in animal models. Methods for the extrapolation of effective dosages in mice, and other animals, to humans are known in the art; see, for example, U.S. Pat. No. 4,938,949, the disclosures of which are hereby incorporated herein by reference, in their entireties. Additionally, useful dosages can be determined by measuring the rate of hydrolysis for a given polymer under various physiological conditions. The amount of a polymer required for use in treatment will vary not only with the particular polymer selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Combination Therapies

The polymers of the invention are also useful for administering a combination of therapeutic agents to an animal. Such a combination therapy can be carried out, for example, in the following ways: (1) a second therapeutic agent can be dispersed within the polymer matrix of a polymer of the invention, and can be released upon degradation of the polymer; (2) a second therapeutic agent can be appended to a polymer of the invention (i.e. not in the backbone of the polymer) with bonds that hydrolyze to release the second therapeutic agent under physiological conditions; (3) the polymer of the invention can be incorporated with two therapeutic agents into the polymer backbone (e.g. a polymer comprising one or more units of formula (II)) or (4) two polymers of the invention, each with a different therapeutic agent can be administered together (or within a short period of time).

Thus, the invention also provides a pharmaceutical composition comprising a polymer of the invention and a second therapeutic agent that is dispersed within the polymer matrix of a polymer of the invention. The invention also provides a pharmaceutical composition comprising a polymer of the invention having a second therapeutic agent appended to the polymer (e.g. with bonds that will hydrolyze to release the second therapeutic agent under physiological conditions).

The polymers of the invention can also be administered in combination with other therapeutic agents that are effective to treat a given condition to provide a combination therapy. Thus, the invention also provides a method for treating a disease in a mammal comprising administering an effective amount of a combination of a polymer of the invention and another therapeutic agent. The invention also provides a pharmaceutical composition comprising a polymer of the invention, another therapeutic agent, and a pharmaceutically acceptable carrier.

Examples of monomers and polymers of the present invention are provided for some embodiments of the current invention. It can be extended to other species. This selection is not meant to limit the scope of the invention in any way. Other variations in the procedure may be readily apparent to those skilled in the art.

EXAMPLE 1

Chloro-acetic acid 2-(2-chloro-acetoxy)-ethyl ester

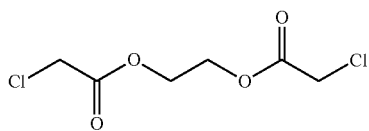 [SMILES: O=C(CCl)OCCOC(=O)CCl]

A solution ethylene glycol (100 grams, 1.611 moles), chloroacetic acid (385 grams, 4.031 moles) and paratoluene sulphonic acid (1 gram) in toluene (750 mL) in a 2 lit 4 neck round bottom flask equipped with a mechanical stirrer, Deanstark apparatus was refluxed for 8 hours, cooled to room temperature. The toluene layer was washed with water (2×300 mL), 5% sodium bicarbonate solution (3×500 mL), water (2×300 mL), dried over sodium sulphate and distilled to get crude 1, which was purified by high vacuum distillation to get pure 1 (242 grams, 69.8%), which slowly crystallized to white crystals m.p: 44° C., $^1$H NMR (CDCl$_3$): δ 4.16 (s, 2H, CH$_2$), 4.85 (s, 2H, CH$_2$).

EXAMPLE 2

(4-Methoxycarbonylmethoxy-phenoxy)-acetic acid methyl ester

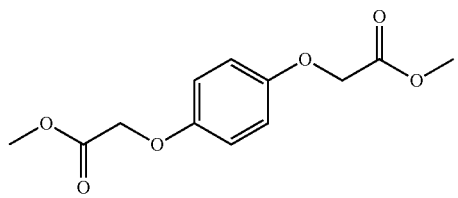

To a mixture of sodium hydride (60%, 92 grams, 2.3 moles) in DMF (400 mL) at 0° C. was carefully added hydroquinone (100 grams, 909 mmol). The mixture was stirred for 30 minutes. Methyl chloro acetate (247 grams, 2.276 moles) was added drop wise, and the mixture was stirred at room temperature for 2 hours. The reaction mixture was carefully quenched into ice water (2 lit). Crude product was filtered, dried, and recrystallised from a mixture of Ethyl acetate: Hexane (1:6) to give pure product (95 grams, 41.1%) as a white powder. M.p: 96-98° C. $^1$H NMR (CDCl$_3$) δ 3.68 (s, 3H, Ester), 4.54 (s, 2H$_2$OCH$_2$), 6.82 (s, 2H, Ar).

EXAMPLE 3

(4-Carboxymethoxy-phenoxy)-acetic acid

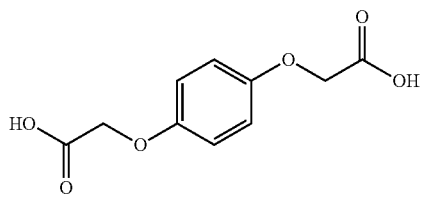 [SMILES: O=C(O)COc1ccc(OCC(=O)O)cc1]

Example 1 (100 grams, 394 mmol) was added to 3.25 M—sodium hydroxide solution (600 mL). The mixture was heated to 70° C. for 20 hours and poured onto ice cold water (1 lit) and the pH adjusted to 1 with concentrated hydrochloric acid. The crude product was filtered, dried, and recrystallised from DMF by precipitating with water to give pure compound (60 grams, 67.4%) as a white powder. Mp: 254-256.5° C. $^1$H NMR (CDCl$_3$+DMSO, d$_6$) 4.44 (s, 2H, OCH$_2$), 6.72 (s, 2H, Ar).

EXAMPLE 4

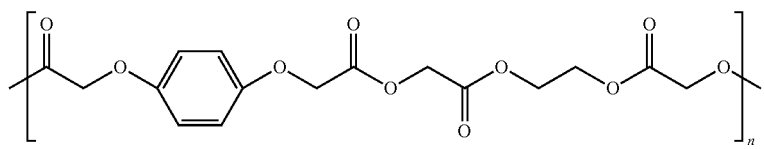

To a solution of Example 3 (10 grams, 44.24 mmoles), trietylamine (13.4 grams, 132.42 mmoles) in dry dimethylformamide (100 mL) was added chloroacetic acid 2-(2-chloro-acetoxy)-ethyl ester (9.515 grams, 44.24 mmoles), Example 1, and stirred at room temperature for 30 hours. The solid triethylamine hydrochloride is filtered and to the filtrate, cold water (300 mL) was added. The precipitated polymer was filtered, slurried with ethyl acetate, filtered, and dried under vacuum at 50° C. to yield the polymer (10 grams) as a white powder. M.p: 76.5-87° C. The molecular weights of this polymer was characterized by GPC and the results are summarized below:

Weight-average molecular weight: Mw=16,856

Number average-average molecular weight: Mn=13,456

Polydispersity Index (Mw/Mn): P.I=1.25 z-Average molecular weight: Mz=20,597

Hydrolysis

| Polymer | 0.5 grams |
|---|---|
| Aldrich pH 9 buffer | 50 mL |
| Temperature | 100° C. |

Hydrolyzed in 5 hours

EXAMPLE 5

[3-(4-Methoxycarbonylmethoxy-phenyl)-4-oxo-4H-chromen-7-yloxy]-acetic acid methyl ester

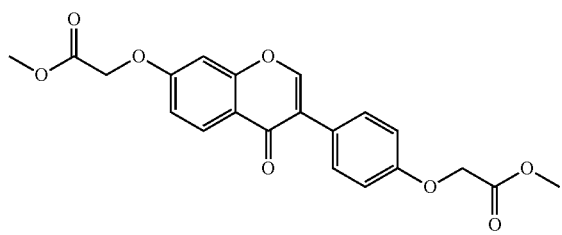

To a mixture of Daidzein (20 grams, 79 mmol), anhydrous K$_2$CO$_3$ (100 grams, 723 mmol), sodium iodide (8 grams, 53.4 mmol), and disodium phosphate (8 grams, 57 mmol) in anhydrous acetone (600 mL) was added methyl chloro acetate (29.2 grams, 269 mmol). The mixture was refluxed for 6 hours. Acetone was distilled and water (600 mL) added. The crude product was filtered, dried, and recrystallised from toluene to give pure product (22 grams, 70%) as a white powder. M.p: 163-165.7° C. $^1$HNMR (CDCl$_3$) δ 3.69 (s, 3H, ester), 3.80 (s, 3H, Ester), 4.68 (s, 2H, OCH$_2$), 4.79 (s, 2H, OCH$_2$), 6.83 (d, 1H, Ar), 6.88 (dd, 2H, B-ring), 7.02 (dd, 1H, Ar), 7.46 (dd, 2H, B-ring), 8.00 (s, 1H, pyran), 8.18 (dd, 1H, Ar).

EXAMPLE 6

[3-(4-Carboxymethoxy-phenyl)-4-oxo-4H-chromen-7-yloxy]-acetic acid

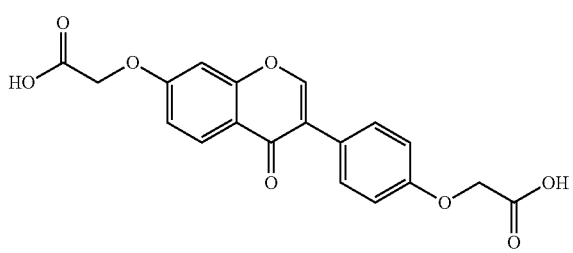 [SMILES: O=C(O)COc1ccc(-c2coc3cc(OCC(=O)O)ccc3c2=O)cc1]

A mixture of Example 4 (45 grams, 113.5 mmol) and concentrated HCl (250 mL) was heated at 90° C. for 5 hours. The reaction mixture was cooled to room temperature and poured onto ice water (250 mL), filtered, washed with water and methanol, and dried. The crude product was recrystallised from dimethyl formamide and precipitated with water to give pure product (36 grams, 86.1%) as a white powder. M.p: 270-272.2° C.

EXAMPLE 7

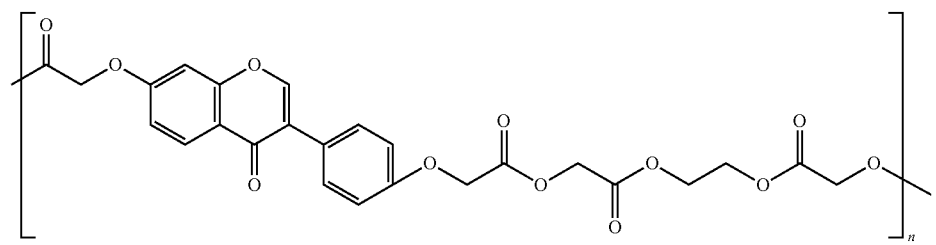

To a solution of Example 6 (10 grams, 27.02 mmoles) and triethylamine (8.20 grams, 81.03 mmoles) in dry dimethylformamide (100 mL) was added chloroacetic acid 2-(2-chloro-acetoxy)-ethyl ester (5.811 grams, 27.02 mmoles), Example 1. The mixture was stirred at room temperature for 30 hours. The solid triethylamine hydrochloride was filtered and to the filtrate, cold water (300 mL) was added. The precipitated polymer was filtered, slurried with methanol, filtered, and dried under vacuum at 50° C. to get the polymer (11 grams) as white powder. M.p: 80-120° C. The molecular weights of this polymer was characterized by GPC and the results are summarized below:

Weight-average molecular weight: Mw=28,954

Number average-average molecular weight: Mn=21,238

Polydispersity Index (Mw/Mn): P.I=1.36 z-Average molecular weight: Mz=36,256

Hydrolysis

| Polymer | 0.5 grams |
|---|---|
| Aldrich pH 9 buffer | 50 mL |
| Temperature | 100° C. |

Hydrolyzed in 6 hours

EXAMPLE 8

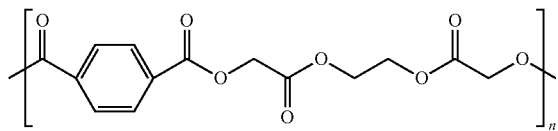

To a solution of terephthallic acid (10 grams, 60.15 mmoles) and triethylamine (15.3 grams, 151.20 mmoles) in dry dimethylformamide (100 mL) was added chloroacetic acid 2-(2-chloro-acetoxy)-ethyl ester (12.94 grams, 60.19 mmoles), example 1. The mixture was stirred at room temperature for 20 hours. The solid triethylamine hydrochloride is filtered and to the filtrate, cold water (300 mL) was added. The precipitated polymer was filtered slurried with methanol, filtered and dried under vacuum at 50° C. to get polymer 41 (14 grams) as off white powder. M.p: 180-189° C.

Hydrolysis

| Polymer | 0.5 grams |
|---|---|
| Aldrich pH 9 buffer | 50 mL |
| Temperature | 100° C. |

Hydrolyzed in 6 hours

EXAMPLE 9

Chloro-acetic acid 4-(2-chloro-acetoxy)-phenyl ester

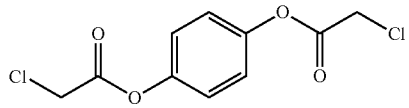 [SMILES: O=C(CCl)Oc1ccc(OC(=O)CCl)cc1]

A mixture of hydroquinone (50 grams, 454.09 mmol) and chloroacetyl chloride (150 mL) was refluxed for 48 hours. Excess chloroacetyl chloride was distilled off, and the residue taken into ice water, filtered, dried, and recrystallised from ethyl acetate:hexane (1:6) to get pure product (55 grams, 46%) as a white fluffy powder. M.p: 127-128° C. $^1$H NMR (CDCl$_3$) δ 4.20 (s, 25H, CH$_2$), 7.24 (s, 2H, Ar).

EXAMPLE 10

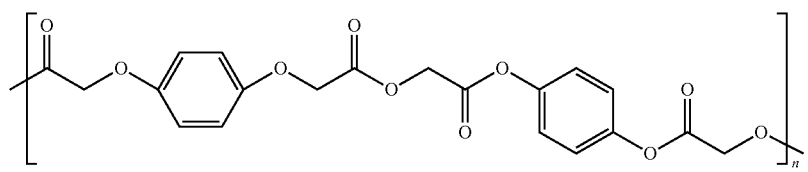

To a mixture of Example 3 (8.6 grams, 38.02 mmol) and triethylamine (13.43 grams, 132.72 mmol) in dry dimethyl formamide (100 mL) was added chloroacetic acid 4-(2-chloro-acetoxy)-phenyl ester (10 grams, 38.01 mmol), Example 9. The mixture was stirred at room temperature for 48 hours. The solid triethylamine hydrochloride was filtered off, and the DMF solution was taken into ice water, filtered, dried, slurried in methanol followed by ethyl acetate, and dried under vacuum to get pure polymer (13 grams) as a white powder. M.p: 232-234° C.

EXAMPLE-11

{2-[4-(2-Carboxymethoxy-ethoxy)-phenoxy]-ethoxy}-acetic acid

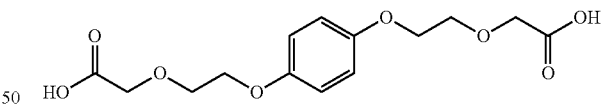

To a suspension of sodium hydride (60%, 132 grams, 3.30 moles) in anhydrous dimethyl formamide (600 mL) under nitrogen atmosphere at 0° C. was added Hydroquinone bis ethanol (150 grams, 756.7 mmoles) in small lots, later stirred at room temperature for one hour. To the above mixture was added a solution of chloroacetic acid (195 grams, 2.06 moles) in anhydrous Dimethyl formamide (300 mL) very cautiously drop wise as the reaction is exothermic. Later the reaction is maintained at 800° C. for one hour and left at room temperature for 16 hours. Reaction mixture carefully poured onto ice (3 kg), extracted with Ethyl acetate (2×500 mL) and organic phase discarded. The aqueous layer pH is adjusted to 2 with 3N-Hydrochloric acid and extracted into ethyl acetate. The ethyl acetate extract was washed with 5% sodium bicarbonate (4×75 mL). The ethyl acetate layer discarded. The aqueous layer washed with ethyl acetate (3×200 mL), acidified with concentrate HCl to pH-2, extracted with ethyl acetate, dried over sodium sulphate, distilled, and precipitated with hexane (500 mL) to get pure 1 (75 grams, 39.6%) as an off white powder. M.p: 112-115.5° C. $^1$H NMR (CDCl$_3$) δ 3.84 (m, 2H, CH$_2$), 4.06 (m, 4H, CH$_2$x$_2$), 6.82 (s, 2H, Ar).

EXAMPLE 12

Polymer of {2-[4-(2-Carboxymethoxy-ethoxy)-phenoxy]-ethoxy}-acetic acid

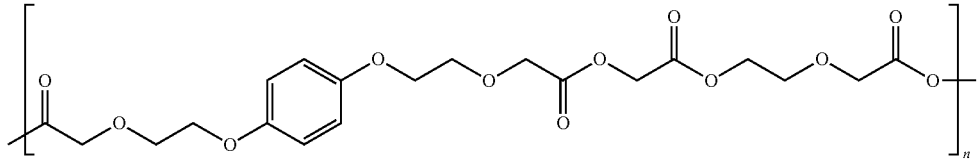

To a mixture of {2-[4-(2-Carboxymethoxy-ethoxy)-phenoxy]-ethoxy}-acetic acid (10 grams, 31.817 mmol) and Example 11, triethylamine (9.656 grams, 95.424 mmol) in dry dimethylformamide (100 mL) was added Example 1 (6.84 grams, 31.81 mmol). The mixture was stirred at room temperature for 96 hours. The solid triethylamine hydrochloride was filtered off and washed with DMF, and the solvent was distilled off under vacuum. The polymer was washed with isopropyl alcohol (6×35 mL) and dried using a high vacuum pump at 40° C. for 4 hours to recover and amber colored viscous syrup.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

[Embodiment 1] A biodegradable polyester of formula III, VI, or XI, or a biodegradable polyamide ester of formula VIII or IX, or a pharmaceutically acceptable salt thereof:

(A)

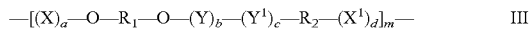   III wherein the polyester of formula III is formed by condensation polymerization of monomers of formula I and II:

   I

   II (B)

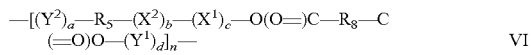   VI wherein the polyester of formula IV is formed by condensation polymerization of monomers of formula IV and V:

   IV

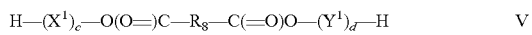   V (C)

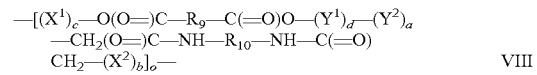   VIII wherein the polyamide ester of formula VIII is formed by condensation polymerization of monomers of formula Va and VII:

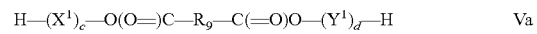   Va

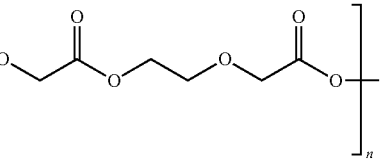

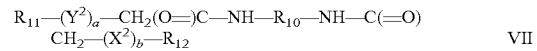   VII (D)

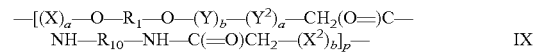   IX wherein the polyamide ester of formula IX is formed by condensation polymerization of monomers of formula I and VII:

   I

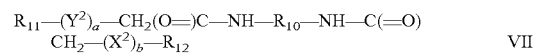   VII (E)

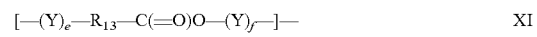   XI wherein the polyester of formula XI is formed by self condensation polymerization of a monomer of formula X:

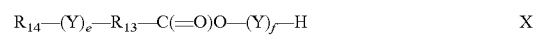   X wherein:

m, n, o, p, and q are each independently an integer from about 5 to about 1000;

R$_1$, R$_5$, R$_9$, and R$_{13}$ are each independently the remaining portion of a biologically active compound;

R$_2$, R$_8$, and R$_{10}$ are each independently the remaining portion of a biologically active compound or non-biologically active compound;

R$_3$, R$_4$, R$_6$, R$_7$, R$_{11}$, R$_{12}$, and R$_{13}$ are each independently selected from Cl, F, Br, and I;

X, X$^1$ and X$^2$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;

Y, Y$^1$, and Y$^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O—(dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;

each y and z is independently an integer from about 2 to about 24;

each a, b, c, and d is independently an integer from about 1 to about 6;
each e is independently an integer from about 1 to about 6; and
each f is independently an integer from about 0 to about 6.

[Embodiment 2] A biodegradable polyester of Embodiment 1 having formula III or a pharmaceutically acceptable salt thereof:

$$-[(X)_a-O-R_1-O-(Y)_b-(Y^1)_c-R_2-(X^1)_d]_m- \quad \text{III}$$

wherein the polyester is formed by condensation polymerization of monomers of formula I and II:

$$H-(X)_a-O-R_1-O-(Y)_b-H \quad \text{I}$$

$$R_3-(Y^1)_c-R_2-(X^1)_d-R_4 \quad \text{II}$$

wherein:
m is an integer from about 5 to about 1000;
$R_1$ is the remaining portion of a biologically active compound;
$R_2$ is the remaining portion of a biologically active compound or non-biologically active compound;
$R_3$ and $R_4$ are independently selected from Cl, F, Br, and I;
X and $X^1$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;
Y and $Y^1$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
each y and z is independently an integer from about 2 to about 24; and
each a, b, c, and d is independently an integer from about 1 to about 6.

[Embodiment 3] A biodegradable polyester of Embodiment 1 having formula VI or a pharmaceutically acceptable salt thereof:

$$-[(Y^2)_a-R_5-(X^2)_b-(X^1)_c-O(O=)C-R_8-C(=O)O-(Y^1)_d]_n- \quad \text{VI}$$

wherein the polyester is formed by condensation polymerization of monomers of formula IV and V:

$$R_6-(Y^2)_a-R_5-(X^2)_b-R_7 \quad \text{IV}$$

$$H-(X^1)_c-O(O=)C-R_8-C(=O)O-(Y^1)_d-H \quad \text{V}$$

wherein:
n is an integer from about 5 to about 1000;
$R_5$ is the remaining portion of a biologically active compound;
$R_6$ and $R_7$ are independently selected from Cl, F, Br, and I;
$R_8$ is the remaining portion of a biologically active compound or non-biologically active compound;
$X^1$ and $X^2$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;
$Y^1$ and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
each y and z is independently an integer from about 2 to about 24; and
each a, b, c, and d is independently an integer from about 1 to about 6.

[Embodiment 4] A biodegradable polyamide ester of Embodiment 1 having formula VIII or a pharmaceutically acceptable salt thereof:

$$-[(X^1)_c-O(O=)C-R_9-C(=O)O-(Y^1)_d-(Y^2)_a-CH_2(O=)C-NH-R_{10}-NH-C(=O)CH_2-(X^2)_b]_o- \quad \text{VIII}$$

wherein the polyamide ester is formed by condensation polymerization of monomers of formula Va and VII:

$$H-(X^1)_c-O(O=)C-R_9-C(=O)O-(Y^1)_d-H \quad \text{Va}$$

$$R_{11}-(Y^2)_a-CH_2(O=)C-NH-R_{10}-NH-C(=O)CH_2-(X^2)_b-R_{12} \quad \text{VII}$$

wherein:
o is an integer from about 5 to about 1000;
$R_9$ is the remaining portion of a biologically active compound;
$R_{10}$ is the remaining portion of a biologically active compound or non-biologically active compound;
$R_{11}$ and $R_{12}$ are independently selected from Cl, F, Br, and I;
$X^1$ and $X^2$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;
$Y^1$ and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
each y and z is independently an integer from about 2 to about 24; and
each a, b, c, and d is independently an integer from about 1 to about 6.

[Embodiment 5] A biodegradable polyamide ester of Embodiment 1 having formula IX or a pharmaceutically acceptable salt thereof:

$$-[(X)_a-O-R_1-O-(Y)_b-(Y^2)_a-CH_2(O=)C-NH-R_{10}-NH-C(=O)CH_2-(X^2)_b]_p- \quad \text{IX}$$

wherein the polyamide ester is formed by condensation polymerization of monomers of formula I and VII:

$$H-(X)_a-O-R_1-O-(Y)_b-H \quad \text{I}$$

$$R_{11}-(Y^2)_a-CH_2(O=)C-NH-R_{10}-NH-C(=O)CH_2-(X^2)_b-R_{12} \quad \text{VII}$$

wherein:
p is an integer from about 5 to about 1000;
$R_1$ is the remaining portion of a biologically active compound;
$R_{10}$ is the remaining portion of a biologically active compound or non-biologically active compound;
$R_{11}$ and $R_{12}$ are independently selected from Cl, F, Br, and I;

X and $X^2$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—; and, Y and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;

each y and z is independently an integer from about 2 to about 24; and each a, b, c, and d is independently an integer from about 1 to about 6.

[Embodiment 6] A biodegradable polyester of Embodiment 1 having formula XI or a pharmaceutically acceptable salt thereof:

[—(Y)$_e$—R$_{13}$—C(=O)O—(Y)$_f$—]$_q$—  XI wherein the polyester is formed by self condensation polymerization of a monomer of formula X:

R$_{14}$—(X)$_e$—R$_{13}$—C(=O)O—(Y)$_f$—H  X wherein:
q is an integer from about 5 to about 1000;
R$_{13}$ is the remaining portion of a biologically active compound;
R$_{14}$ is selected from Cl, F, Br, and I;
Y is independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
each e is independently an integer from about 1 to about 6; and
each f is independently an integer from about 0 to about 6.

[Embodiment 7] A polyester of Embodiment 3, wherein the non-biologically active compound is a dicarboxylic compound selected from:

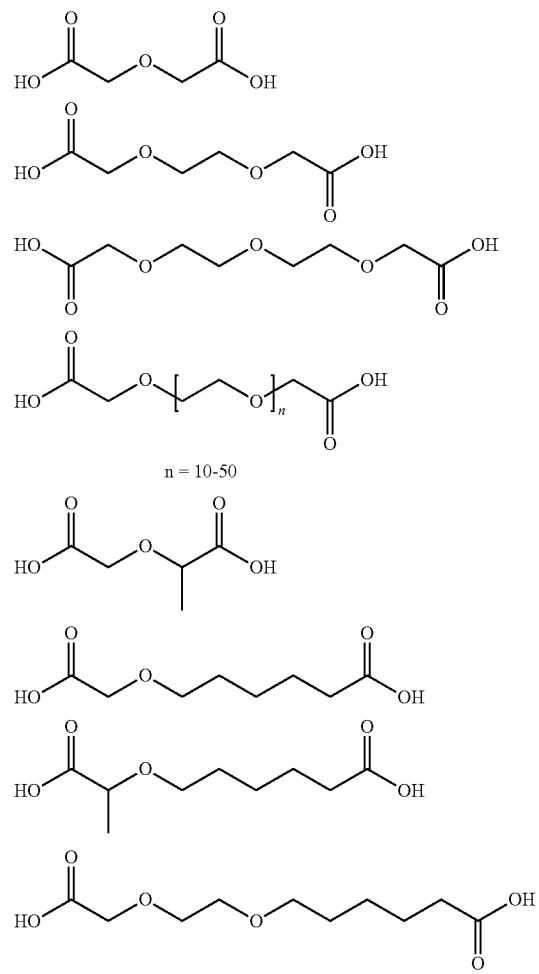

[Embodiment 8] A polyester of Embodiment 2, wherein the non-biologically active compound is a diamino compound selected from:

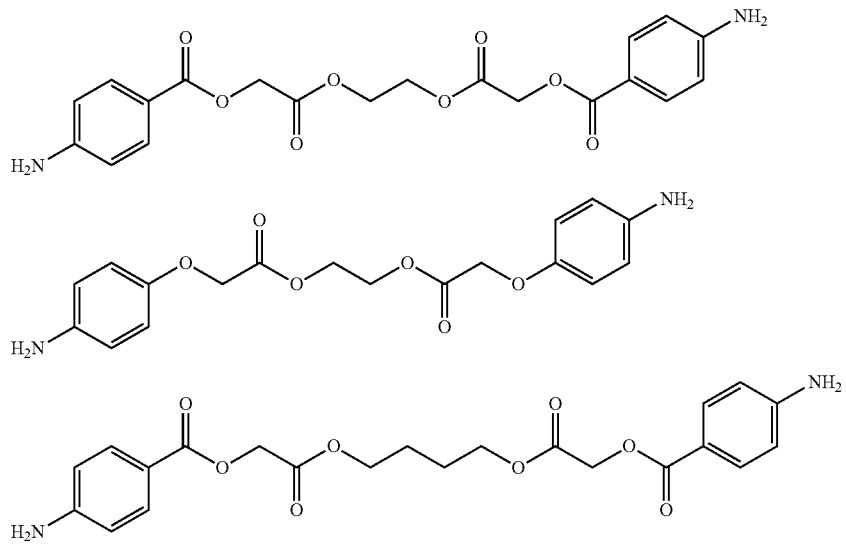

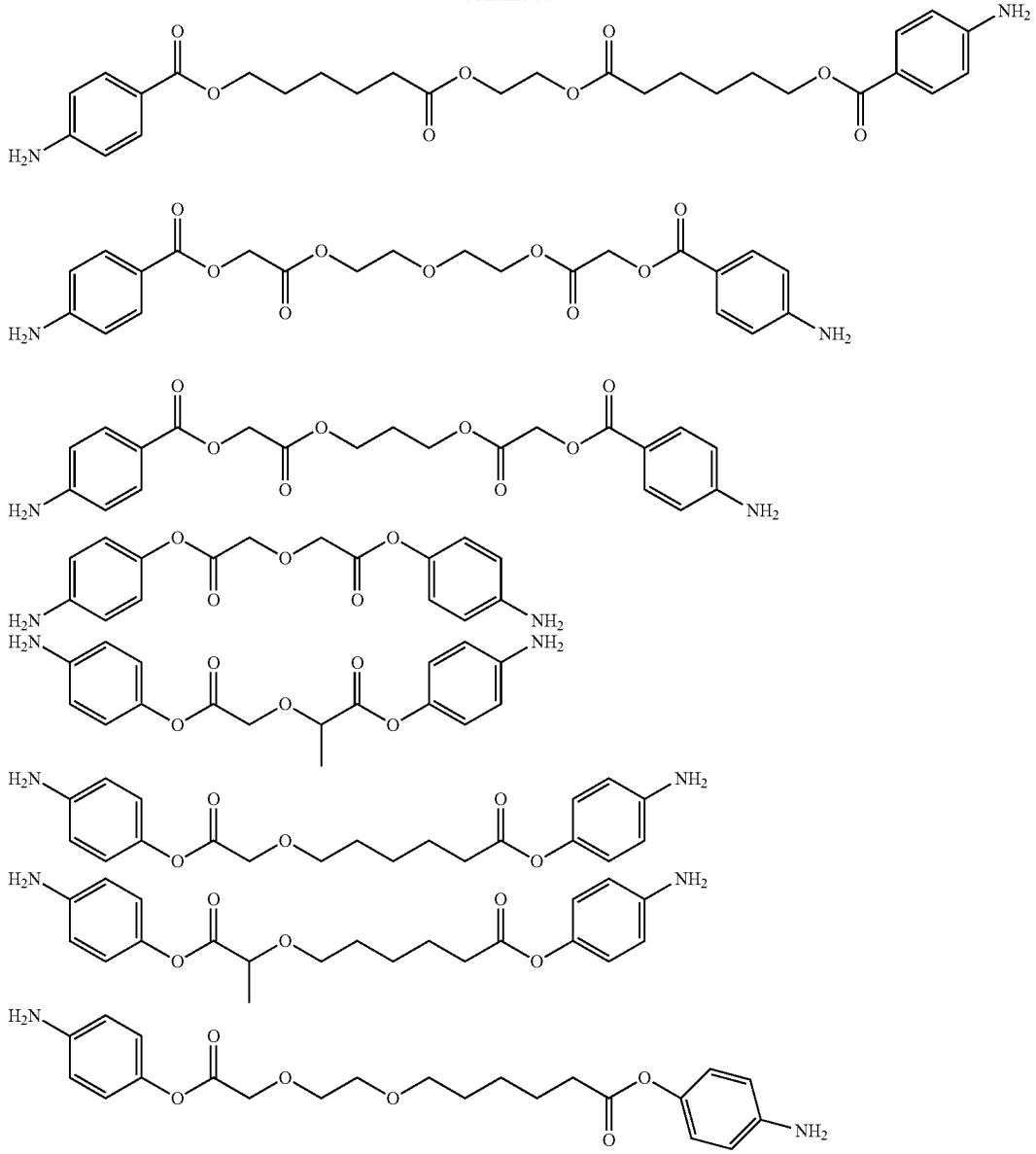
[Embodiment 9] A polyamide ester of Embodiment 4, wherein the non-biologically active compound is a diamino compound selected from:
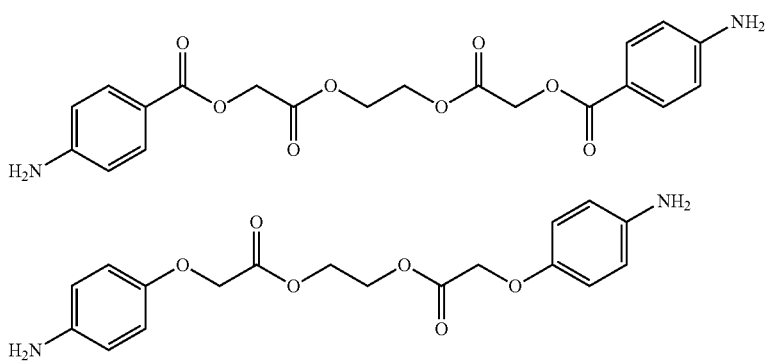

-continued
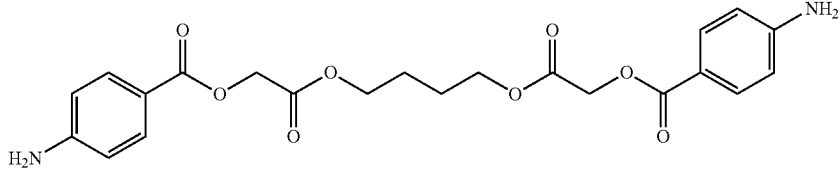
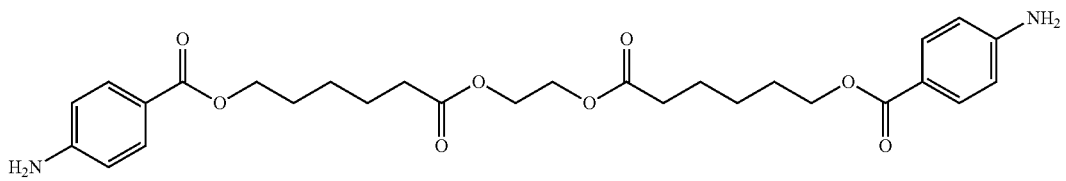
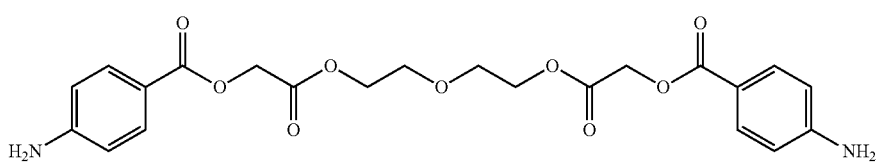
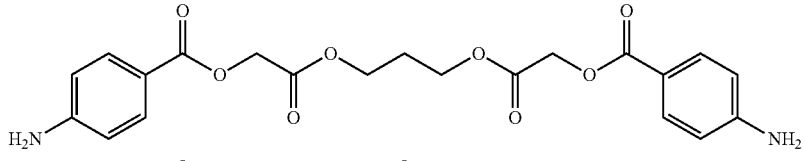
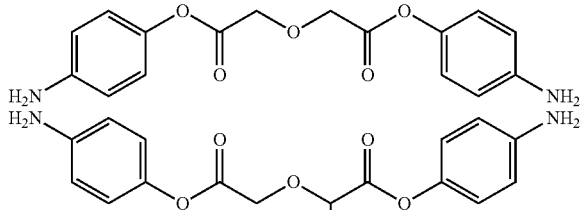
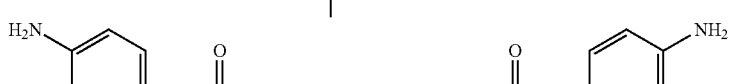
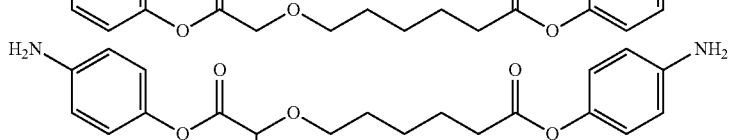
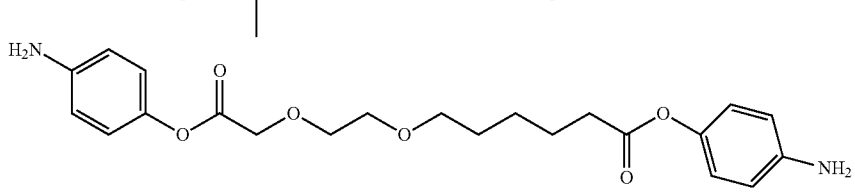
[Embodiment 10] A polyamide ester of Embodiment 5, wherein the non-biologically active compound is a diamino compound selected from:
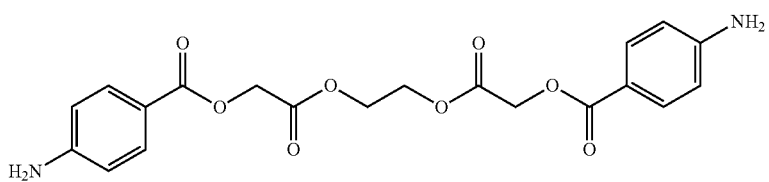

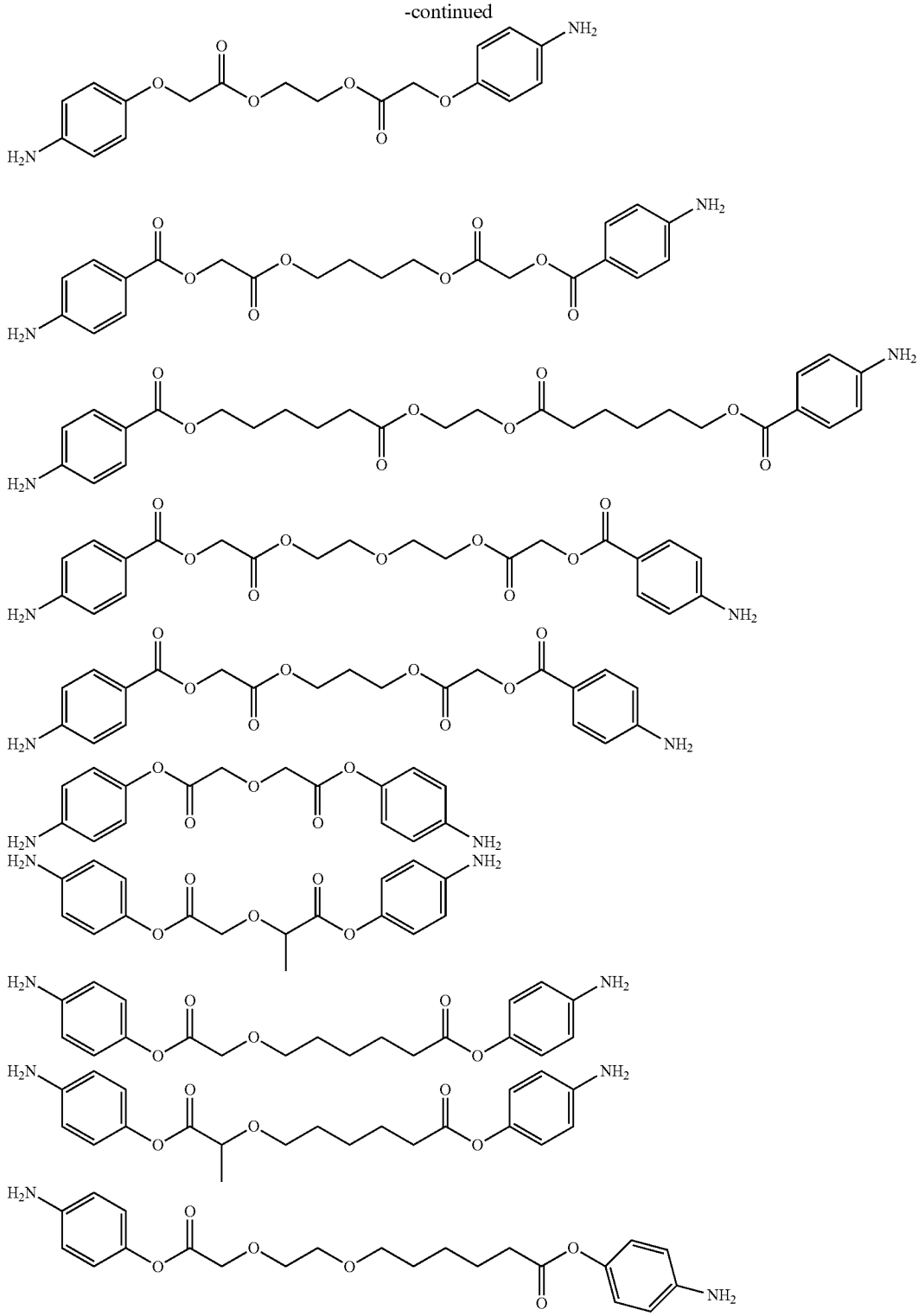

[Embodiment 11] A biodegradable monomer of Embodiment 1, which is selected from a monomer of formula I, II, IV, V, Va, VII, and X.

[Embodiment 12] A composition comprising at least two different polymers, wherein each polymer is independently a polymer according to Embodiment 1, 2, 3, 4, 5, 6, 7, 8, 9, or 10.

[Embodiment 13] A cosmetic composition comprising a cosmetic ingredient and at least one polymer according to Embodiment 1, 2, 3, 4, 5, 6, 7, 8, 9, or 10.

[Embodiment 14] An implantable medical device comprising at least one polymer according to Embodiment 1, 2, 3, 4, 5, 6, 7, 8, 9, or 10.

[Embodiment 15] An implantable medical device of Embodiment 14, wherein the polymer has been further polymerized with a lactone monomer selected from glycolide, lactide, ε-caprolactone, trimethylene carbonate, ether lactones, morpholinediones, and p-dioxanone.

[Embodiment 16] An implantable medical device of Embodiment 14, wherein the device is a stent.

[Embodiment 17] An implantable medical device of Embodiment 16, wherein the polymer has been further polymerized with a lactone monomer selected from glycolide, lactide, ε-caprolactone, trimethylene carbonate, ether lactones, morpholinediones, and p-dioxanone.

[Embodiment 18] An implantable medical device of Embodiment 14, wherein the device is a scaffold for tissue engineer, comprising a porous structure for the attachment and proliferation of cells.

[Embodiment 19] An implantable medical device of Embodiment 18, wherein the polymer has been further polymerized with a lactone monomer selected from glycolide, lactide, ε-caprolactone, trimethylene carbonate, ether lactones, morpholinediones, and p-dioxanone.

[Embodiment 20] A coating for a stent comprising at least one polymer according to Embodiment 1, 2, 3, 4, 5, 6, 7, 8, 9, or 10.

[Embodiment 21] A stent coating of Embodiment 20, wherein the polymer has been further polymerized with a lactone monomer selected from glycolide, lactide, ε-caprolactone, trimethylene carbonate, ether lactones, morpholinediones, and p-dioxanone.

[Embodiment 22] A drug delivery system comprising at least one polymer according to Embodiment 1, 2, 3, 4, 5, 6, 7, 8, 9, or 10 physically admixed with a biologically or pharmacologically active agent.

[Embodiment 23] A drug delivery system wherein the biologically or pharmacologically active agent is physically embedded or dispersed into the polymer and the polymer is in the form of a polymeric matrix.

[Embodiment 24] A suture coating comprising at least one polymer according to Embodiment 1, 2, 3, 4, 5, 6, 7, 8, 9, or 10.

[Embodiment 25] A suture comprising at least one polymer according to Embodiment 1, 2, 3, 4, 5, 6, 7, 8, 9, or 10.

[Embodiment 26] An antimicrobial agent comprising at least one polymer according to Embodiment 1, 2, 3, 4, 5, 6, 7, 8, 9, or 10.

[Embodiment 27] A method for treating a disease in a patient comprising administering to an animal in need of such therapy, an effective amount of at least one polymer according to Embodiment 1, 2, 3, 4, 5, 6, 7, 8, 9, or 10.

[Embodiment 28] A method for producing an analgesic effect in a patient, comprising administering to an animal in need of such therapy, an effective amount of at least one polymer according to Embodiment 1, 2, 3, 4, 5, 6, 7, 8, 9, or 10.

[Embodiment 29] A method for treating cancer in a patient comprising administering to an animal in need of such therapy, an effective amount of at least one polymer according to Embodiment 1, 2, 3, 4, 5, 6, 7, 8, 9, or 10.

[Embodiment 30] A method for producing an anti-inflammatory effect in a patient comprising administering to an animal in need of such therapy, an effective amount of at least one polymer according to Embodiment 1, 2, 3, 4, 5, 6, 7, 8, 9, or 10.

[Embodiment 31] A method for producing an anti-bacterial effect in a patient comprising administering to an animal in need of such therapy, an effective amount of at least one polymer according to Embodiment 1, 2, 3, 4, 5, 6, 7, 8, 9, or 10.

[Embodiment 32] A method for producing an anti-fungal effect in a patient comprising administering to an animal in need of such therapy, an effective amount of at least one polymer according to Embodiment 1, 2, 3, 4, 5, 6, 7, 8, 9, or 10.

[Embodiment 33] A therapeutic method for producing an immunosuppressive effect in a patient comprising administering to an animal in need of such therapy, an effective amount of at least one polymer according to Embodiment 1, 2, 3, 4, 5, 6, 7, 8, 9, or 10.

[Embodiment 34] A method for producing an anti-thrombotic effect in an patient comprising administering to an animal in need of such therapy, an effective amount of at least one polymer according to Embodiment 1, 2, 3, 4, 5, 6, 7, 8, 9, or 10.

[Embodiment 35] A method for treating psoriasis, inflammatory bowel disease, skin cancer, or a brain tumor in an patient, comprising administering to an animal in need of such therapy, an effective amount of at least one polymer according to Embodiment 1, 2, 3, 4, 5, 6, 7, 8, 9, or 10.

[Embodiment 36] A method for producing an anti-infective effect in a patient, comprising administering to an animal in need of such therapy, an effective amount of at least one polymer according to Embodiment 1, 2, 3, 4, 5, 6, 7, 8, 9, or 10.

[Embodiment 37] A method for treating pain in a patient, comprising administering to an animal in need of such therapy, an effective amount of at least one polymer according to Embodiment 1, 2, 3, 4, 5, 6, 7, 8, 9, or 10.

What is claimed is:

1. A composition comprising at least two different polymers, wherein each polymer is independently selected from: a biodegradable polyester of formula III, VI, or XI, or a pharmaceutically acceptable salt thereof:

(A)

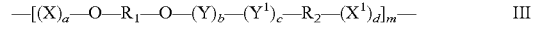

$$-[(X)_a-O-R_1-O-(Y)_b-(Y^1)_c-R_2-(X^1)_d]_m- \quad \text{III}$$

wherein the polyester of formula III is formed by condensation polymerization of monomers of formula I and II:

$$H-(X)_a-O-R_1-O-(Y)_b-H \quad \text{I}$$

$$R_3-(Y^1)_c-R_2-(X^1)_d-R_4 \quad \text{II}$$

B

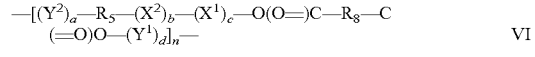

$$-[(Y^2)_a-R_5-(X^2)_b-(X^1)_c-O(O=)C-R_8-C(=O)O-(Y^1)_d]_n- \quad \text{VI}$$

wherein the polyester of formula IV is formed by condensation polymerization of monomers of formula IV and V:

$$R_6-(Y^2)_a-R_5-(X^2)_b-R_7 \quad \text{IV}$$

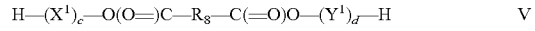

$$H-(X^1)_c-O(O=)C-R_8-C(=O)O-(Y^1)_d-H \quad \text{V}$$

(E)

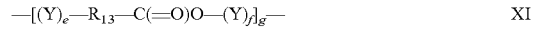

$$-[(Y)_e-R_{13}-C(=O)O-(Y)_f]_q- \quad \text{XI}$$

wherein the polyester of formula XI is formed by self condensation polymerization of a monomer of formula X:

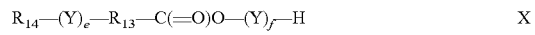

$$R_{14}-(Y)_e-R_{13}-C(=O)O-(Y)_f-H \quad \text{X}$$

wherein:

m, n, and q are each independently an integer from about 5 to about 1000;

$R_1$, $R_5$, and $R_{13}$ are each independently the remaining portion of a biologically active compound;

$R_2$ and $R_8$ are each independently the remaining portion of a biologically active compound or non-biologically active compound;

$R_3$, $R_4$, $R_6$, $R_7$, and $R_{14}$ are each independently selected from Cl, F, Br, and I;

X, $X^1$, and $X^2$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)(OCH$_2$CH$_2$)$_z$—;

Y, $Y^1$, and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;

each y and z is independently an integer from about 2 to about 24;

each a, b, c, and d is independently an integer from about 1 to about 6;

each e is independently an integer from about 1 to about 6; and each f is independently an integer from about 0 to about 6.

2. A cosmetic composition comprising a cosmetic ingredient and at least one polymer selected from: a biodegradable polyester of formula III, VI, or XI, or a pharmaceutically acceptable salt thereof:

(A)

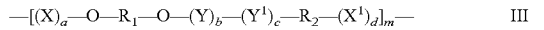   III wherein the polyester of formula III is formed by condensation polymerization of monomers of formula I and II:

   I

   II (B)

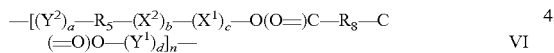   VI wherein the polyester of formula IV is formed by condensation polymerization of monomers of formula IV and V:

   IV

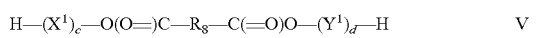   V (E)

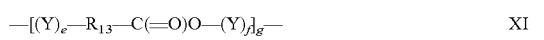   XI wherein the polyester of formula XI is formed by self condensation polymerization of a monomer of formula X:

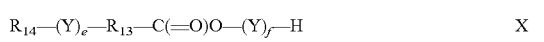   X wherein:

m, n, and q are each independently an integer from about 5 to about 1000;

$R_1$, $R_5$, and $R_{13}$ are each independent the remaining portion of a biologically active compound;

$R_2$ and $R_8$ are each independently the remaining portion of a biologically active compound or non-biologically active compound;

$R_3$, $R_4$, $R_6$, $R_7$, and $R_{14}$ are each independent selected from Cl, F, Br, and I;

X, $X^1$, and $X^2$ are independent at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$—(OCH$_2$CH$_2$)$_z$—;

Y, $Y^1$, and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;

each y and z is independently an integer from about 2 to about 24;

each a, b, c, and d is independently an integer from about 1 to about 6;

each e is independently an integer from about 1 to about 6; and each f is independently an integer from about 0 to about 6.

3. An implantable medical device or coating, comprising at least one polymer selected from: a biodegradable polyester of formula III, VI, or XI, or a pharmaceutically acceptable salt thereof:

(A)

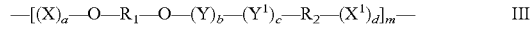   III wherein the polyester of formula III is formed by condensation polymerization of monomers of formula I and II:

   I

   II (B)

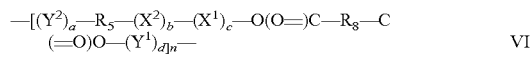   VI wherein the polyester of formula IV is formed by condensation polymerization of monomers of formula IV and V:

   IV

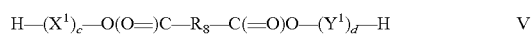   V (E)

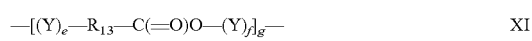   XI wherein the polyester of formula XI is formed by self condensation polymerization of a monomer of formula X:

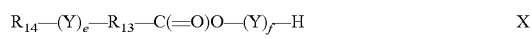   X wherein:

m, n, and q are each independently an integer from about 5 to about 1000;

$R_1$, $R_5$, and $R_{13}$ are each independent the remaining portion of a biologically active compound;

$R_2$ and $R_8$ are each independently the portion of a biologically active compound or non-biologically active compound;

$R_3$, $R_4$, $R_6$, $R_7$, and $R_{14}$ are each independent selected from Cl, F, Br, and I;

X, $X^1$, and $X^2$ are independent at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;

Y, $Y^1$, and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;

each y and z is independently an integer from about 2 to about 24;

each a, b, c, and d is independently an integer from about 1 to about 6;

each e is independently an integer from about 1 to about 6; and each f is independently an integer from about 0 to about 6.

4. An implantable medical device or coating of claim 3, wherein the polymer has been further polymerized with a lactone monomer selected from glycolide, lactide, ε-caprolactone, trimethylene carbonate, ether lactones, morpholinediones, and p-dioxanone.

5. An implantable medical device or coating of claim 3, wherein the device is a stent.

6. An implantable medical device or coating of claim 5, wherein the polymer has been further polymerized with a lactone monomer selected from glycolide, lactide, ε-caprolactone, trimethylene carbonate, ether lactones, morpholinediones, and p-dioxanone.

7. An implantable medical device or coating of claim 3, wherein the device is a scaffold for tissue engineer comprising a porous structure for the attachment and proliferation of cells.

8. An implantable medical device or coating of claim 7, wherein the polymer has been further polymerized with a lactone monomer selected from glycolide, lactide, ε-caprolactone, trimethylene carbonate, ether lactones, morpholinediones, and p-dioxanone.

9. An implantable medical device or coating of claim 3, wherein the device is a coating for a stent.

10. An implantable medical device or coating of claim 9, wherein the polymer has been further polymerized with a lactone monomer selected from glycolide, lactide, ε-caprolactone, trimethylene carbonate, ether lactones, morpholinediones, and p-dioxanone.

11. An implantable medical device or coating of claim 3, wherein the coating is a suture coating.

12. An implantable medical device or coating of claim 3, wherein the device is a suture.

13. An implantable medical device or coating of claim 3, wherein the polymer is a biodegradable polyester having formula III or a pharmaceutically acceptable salt thereof:

$$-[(X)_a-O-R_1-O-(Y)^b-(Y^1)_c-R_2-(X^1)_d]_m-\qquad \text{III.}$$

14. An implantable medical device or coating of claim 3, wherein the polymer is a biodegradable polyester having formula VI or a pharmaceutically acceptable salt thereof:

$$-[(Y^2)_a-R_5-(X^2)_b-(X^1)_c-O(O=)C-R_8-C(=O)O-(Y^1)_d]_n-\qquad \text{VI.}$$

15. An implantable medical device or coating of claim 3, wherein the polymer is a biodegradable polyester having formula XI or a pharmaceutically acceptable salt thereof:

$$-[(Y)_e-R_{13}-C(=O)O-(Y)_f]_g-\qquad \text{XI.}$$

16. An implantable medical device or coating of claim 3, wherein the polymer is a biodegradable polyester of claim 14, wherein the non-biologically active compound is a dicarboxylic compound selected from:

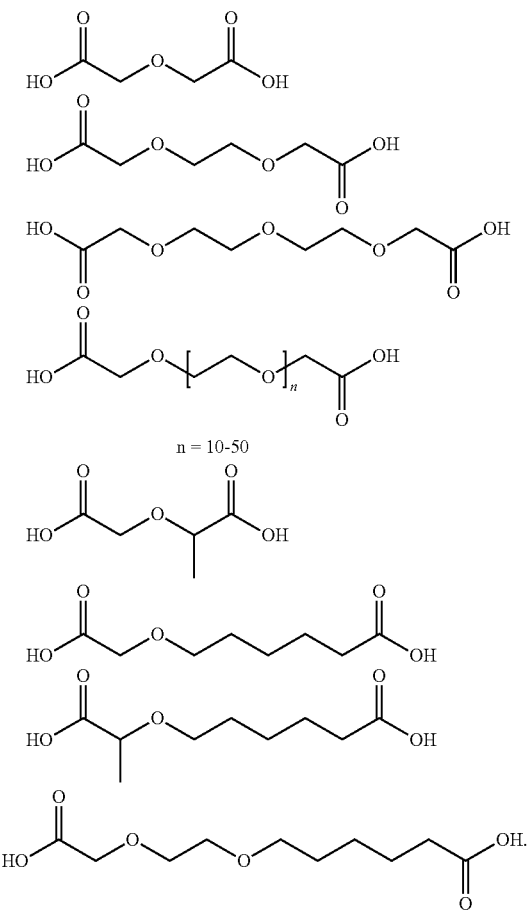

17. A drug delivery system comprising at least one polymer according to claim 1 physically admixed with a biologically or pharmacologically active agent, wherein the polymer is selected from: a biodegradable polyester of formula III, VI, or XI, or a pharmaceutically acceptable salt thereof:

(A)

$$-[(X)_a-O-R_1-O-(Y)_b-(Y^1)_c-R_2-(X^1)_d]_m-\qquad \text{III}$$

wherein the polyester of formula III is formed by condensation polymerization of monomers of formula I and II:

$$H-(X)_a-O-R_1-O-(Y)_b-H\qquad \text{I}$$

$$R_3-(Y^1)_c-R_2-(X^1)_d-R_4\qquad \text{II}$$

(B)

$$-[(Y^2)_a-R_5-(X^2)_b-(X^1)_c-O(O=)C-R_813\\C(=O)O-(Y^1)_d]_n-\qquad \text{VI}$$

wherein the polyester of formula IV is formed by condensation polymerization of monomers of formula IV and V:

$$R_6-(Y^2)_a-R_5-(X^2)_b-R_7 \quad \text{IV}$$

$$H-(X^1)_c-O(O=)C-R_8-C(=O)O-(Y^1)_d-H \quad \text{V}$$

(E)

$$-[(Y)_e-R_{13}-C(=O)O-(Y)_f]_g- \quad \text{XI}$$

wherein the polyester of formula XI is formed by self condensation polymerization of a monomer of formula X:

$$R_{14}-(Y)_e-R_{13}-C(=O)O-(Y)_f-H \quad \text{X}$$

wherein:
 m, n, and q are each independently an integer from about 5 to about 1000;
 $R_1$, $R_5$, and $R_{13}$ are each independent the remaining portion of a biologically active compound;
 $R_2$ and $R_8$ are each independently the remaining portion of a biologically active compound or non-biologically active compound;
 $R_3$, $R_4$, $R_6$, $R_7$, and $R_{14}$ are each independent selected from Cl, F, Br, and I;
 X, $X^1$, and $X^2$ are independent at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;
 Y, $Y^1$, and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
 each y and z is independently an integer from about 2 to about 24;
 each a, b, c, and d is independently an integer from about 1 to about 6;
 each e is independently an integer from about 1 to about 6; and
 each f is independently an integer from about 0 to about 6.

18. A drug delivery system of claim 17, wherein the biologically or pharmacologically active agent is physically embedded or dispersed into the polymer and the polymer is in the form of a polymeric matrix.

19. An antimicrobial agent comprising at least one polymer selected from: a biodegradable polyester of formula III, VI, or XI, or a pharmaceutically acceptable salt thereof:

(A)

$$-[(X)_a-O-R_1-O-(Y)_b-(Y^1)_c-R_2-(X^1)_d]_m- \quad \text{III}$$

wherein the polyester of formula III is formed by condensation polymerization of monomers of formula I and II:

$$H-(X)_a-O-R_1-O-(Y)_b-H \quad \text{I}$$

$$R_3-(Y^1)_c-R_2-(X^1)_d-R_4 \quad \text{II}$$

(B)

$$-[(Y^2)_a-R_5-(X^2)_b-(X^1)_c-O(O=)C-R_8-C(=O)O-(Y^1)_d]_n- \quad \text{VI}$$

wherein the polyester of formula IV is formed by condensation polymerization of monomers of formula IV and V:

$$R_6-(Y^2)_a-R_5-(X^2)_b-R_7 \quad \text{IV}$$

$$H-(X^1)_c-O(O=)C-R_8-C(=O)O-(Y^1)_d-H \quad \text{V}$$

(E)

$$-[(Y)_e-R_{13}-C(=O)O-(Y)_f]_g- \quad \text{XI}$$

wherein the polyester of formula XI is formed by self condensation polymerization of a monomer of formula X:

$$R_{14}-(Y)_e-R_{13}-C(=O)O-(Y)_f-H \quad \text{X}$$

wherein:
 m, n, and q are each independently an integer from about 5 to about 1000;
 $R_1$, $R_5$, and $R_{13}$ are each independent the remaining portion of a biologically active compound;
 $R_2$ and $R_8$ are each independently the remaining portion of a biologically active compound or non-biologically active compound;
 $R_3$, $R_4$, $R_6$, $R_7$, and $R_{14}$ are each independent selected from Cl, F, Br, and I;
 X, $X^1$, and $X^2$ are independent at each occurrence —OC(=O)CH$_2$— (inverse glycolic acid moiety), —CH(CH$_3$)C(=O)O— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;
 Y, $Y^1$, and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
 each y and z is independently an integer from about 2 to about 24;
 each a, b, c, and d is independently an integer from about 1 to about 6;
 each e is independently an integer from about 1 to about 6; and
 each f is independently an integer from about 0 to about 6.

20. A method for treating a disease in a patient, comprising administering to an animal in need of such therapy, an effective amount of at least one polymer selected from: a biodegradable polyester of formula III, VI, or XI, or a pharmaceutically acceptable salt thereof:

(A)

$$-[(X)_a-O-R_1-O-(Y)_b-(Y^1)_c-R_2-(X^1)_d]_m- \quad \text{III}$$

wherein the polyester of formula III is formed by condensation polymerization of monomers of formula I and II:

$$H-(X)_a-O-R_1-O-(Y)_b-H \quad \text{I}$$

$$R_3-(Y^1)_c-R_2-(X^1)_d-R_4 \quad \text{II}$$

(B)

$$-[(Y^2)_a-R_5-(X^2)_b-(X^1)_c-O(O=)O-(Y^1)_d]_n- \quad \text{VI}$$

wherein the polyester of formula IV is formed by condensation polymerization of monomers of formula IV and V:

$$R_6-(Y^2)_a-R_5-(X^2)_b-R_7 \quad \text{IV}$$

$$H-(X^1)_c-O(O=)C-R_8-C(=O)O-(Y^1)_d-H \quad \text{V}$$

(E)

$$-[(Y)_e-R_{13}-C(=O)O-(Y)_f]_g- \quad \text{XI}$$

wherein the polyester of formula XI is formed by self condensation polymerization of a monomer of formula X:

$$R_{14}-(Y)_e-R_{13}-C(=O)O-(Y)_f-H \qquad X$$

wherein:
  m, n, and q are each independently an integer from about 5 to about 1000;
  $R_1$, $R_5$, and $R_{13}$ are each independent the remaining portion of a biologically active compound;
  $R_2$ and $R_8$ are each independently the remaining portion of a biologically active compound or non-biologically active compound;
  $R_3$, $R_4$, $R_6$, $R_7$, and $R_{14}$ are each independently selected from Cl, F, Br, and I;
  X, $X^1$, and $X^2$ are independent at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;
  Y, $Y^1$, and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
  each y and z is independently an integer from about 2 to about 24;
  each a, b, c, and d is independently an integer from about 1 to about 6;
  each e is independently an integer from about 1 to about 6; and
  each f is independently an integer from about 0 to about 6.

21. A method of claim 20, wherein the disease is cancer.

22. A method of claim 20, wherein the disease is selected from psoriasis, inflammatory bowel disease, skin cancer, and a brain tumor.

23. A method for producing an effect in a patient comprising administering to an animal in need of such therapy, an effective amount of at least one polymer selected from: a biodegradable polyester of formula III, VI, or XI, or a pharmaceutically acceptable salt thereof and the effect being selected from an analgesic effect, anti-inflammatory effect, anti-bacterial effect, an anti-fungal effect, an immunosuppressive effect, an anti-thrombotic effect, and an anti-infective effect, wherein:

(A)

$$-[(X)_a-O-R_1-O-(Y)^b-(Y^1)_c-R_2-(X^1)_d]_m- \qquad III$$

wherein the polyester of formula III is formed by condensation polymerization of monomers of formula I and II:

$$H-(X)_a-O-R_1-O-(Y)_b-H \qquad I$$

$$R_3-(Y^1)_c-R_2-(X^1)_d-R_4 \qquad II$$

(B)

$$-[(Y^2)_a-R_5-(X^2)_b-(X^1)_c-O(O=)C-R_8-C(=O)O-(Y^1)_d]_n- \qquad VI$$

wherein the polyester of formula IV is formed by condensation polymerization of monomers of formula IV and V:

$$R_6-(Y^2)_a-R_5-(X^2)_b-R_7 \qquad IV$$

$$H-(X^1)_c-O(O=)C-R_8-C(=O)O-(Y^1)_d-H \qquad V$$

(E)

$$-[(Y)_e-R_{13}-C(=O)O-(Y)_f]_g- \qquad XI$$

wherein the polyester of formula XI is formed by self condensation polymerization of a monomer of formula X:

$$R_{14}-(Y)_e-R_{13}-C(=O)O-(Y)_f-H \qquad X$$

wherein:
  m, n, and q are each independently an integer from about 5 to about 1000;
  $R_1$, $R_5$, and $R_{13}$ are each independent the remaining portion of a biologically active compound;
  $R_2$ and $R_8$ are each independently the remaining portion of a biologically active compound or non-biologically active compound;
  $R_3$, $R_4$, $R_6$, $R_7$, and $R_{14}$ are each independent selected from Cl, F, Br, and I;
  X, $X^1$, and $X^2$ are independently at each occurrence —OC(=O)CH$_2$— (inverse glycolic acid moiety), —OC(=O)CH(CH$_3$)— (inverse lactic acid moiety), —OC(=O)CH$_2$OCH$_2$CH$_2$— (inverse dioxanone acid moiety), —OC(=O)CH$_2$CH$_2$CH$_2$CH$_2$CH$_2$— (inverse caprolactone acid moiety), —OC(=O)(CH$_2$)$_y$—, or —OC(=O)CH$_2$(OCH$_2$CH$_2$)$_z$—;
  Y, $Y^1$, and $Y^2$ are independently at each occurrence —CH$_2$C(=O)O— (glycolic acid moiety), —CH(CH$_3$)C(=O)O— (lactic acid moiety), —CH$_2$CH$_2$OCH$_2$C(=O)O— (dioxanone moiety), —CH$_2$CH$_2$CH$_2$CH$_2$CH$_2$C(=O)O— (caprolactone moiety), —(CH$_2$)$_y$C(=O)O—, or —(CH$_2$CH$_2$O)$_z$CH$_2$C(=O)O—;
  each y and z is independently an integer from about 2 to about 24;
  each a, b, c, and d is independently an integer from about 1 to about 6;
  each e is independently an integer from about 1 to about 6; and
  each f is independently an integer from about 0 to about 6.

24. A method of claim 23, wherein the effect is an anti-inflammatory effect.

25. A method of claim 23, wherein the effect is an anti-bacterial effect.

26. A method of claim 23, wherein the effect is an anti-fungal effect.

27. A method of claim 23, wherein the effect is an immunosuppressive effect.

28. A method of claim 23, wherein the effect is an anti-thrombotic effect.

29. A method of claim 23, wherein the effect is an anti-infective effect.

30. A method of claim 23, wherein the effect is an analgesic effect.

* * * * *